United States Patent
Rodrigo et al.

(10) Patent No.: US 12,221,492 B2
(45) Date of Patent: *Feb. 11, 2025

(54) MUTATED IMMUNOGLOBULIN-BINDING POLYPEPTIDES

(71) Applicant: Cytiva BioProcess R&D AB, Uppsala (SE)

(72) Inventors: Gustav Rodrigo, Uppsala (SE); Tomas Bjorkman, Uppsala (SE); Mats Ander, Uppsala (SE)

(73) Assignee: Cytiva BioProcess R&D AB, Uppsala (SE)

(*) Notice: Subject to any disclaimer, the term of this patent is extended or adjusted under 35 U.S.C. 154(b) by 377 days.

This patent is subject to a terminal disclaimer.

(21) Appl. No.: 17/149,830

(22) Filed: Jan. 15, 2021

(65) Prior Publication Data

US 2021/0147577 A1    May 20, 2021

Related U.S. Application Data

(63) Continuation of application No. 15/525,688, filed as application No. PCT/EP2015/076642 on Nov. 16, 2015, now Pat. No. 11,566,082.

(30) Foreign Application Priority Data

Nov. 17, 2014 (SE) .................................. 1451376-6
Jun. 12, 2015 (GB) .................................. 1510261
Jun. 12, 2015 (GB) .................................. 1510263

(51) Int. Cl.

| C07K 16/46 | (2006.01) |
|---|---|
| B01D 15/38 | (2006.01) |
| B01J 20/289 | (2006.01) |
| B01J 20/32 | (2006.01) |
| C07K 1/22 | (2006.01) |
| C07K 14/31 | (2006.01) |
| C07K 16/00 | (2006.01) |
| C07K 16/06 | (2006.01) |

(52) U.S. Cl.
CPC .......... *C07K 16/46* (2013.01); *B01D 15/3809* (2013.01); *B01J 20/289* (2013.01); *B01J 20/3219* (2013.01); *B01J 20/3274* (2013.01); *C07K 1/22* (2013.01); *C07K 14/31* (2013.01); *C07K 16/00* (2013.01); *C07K 16/065* (2013.01)

(58) Field of Classification Search
None
See application file for complete search history.

(56) References Cited

U.S. PATENT DOCUMENTS

| 4,704,366 A | 11/1987 | Juarez-Salinas et al. |
|---|---|---|
| 4,708,714 A | 11/1987 | Larsson et al. |
| 4,801,687 A | 10/1989 | Ngo |
| 4,933,435 A | 6/1990 | Ngo |
| 5,011,686 A | 4/1991 | Pang |
| 5,084,398 A | 1/1992 | Huston et al. |
| 5,143,844 A | 9/1992 | Abrahmsen et al. |
| 5,476,786 A | 12/1995 | Huston |
| 5,831,012 A | 11/1998 | Nilsson et al. |
| 6,127,526 A | 10/2000 | Blank |
| 6,207,804 B1 | 3/2001 | Huston et al. |
| 6,399,750 B1 | 6/2002 | Johansson |
| 6,602,990 B1 | 8/2003 | Berg |
| 6,870,034 B2 | 3/2005 | Breece et al. |
| 7,220,356 B2 | 5/2007 | Thommes et al. |
| 7,396,467 B2 | 7/2008 | Berg et al. |
| 7,566,565 B2 | 7/2009 | Peters et al. |
| 7,709,209 B2 | 5/2010 | Hober et al. |
| 7,714,111 B2 | 5/2010 | Sun et al. |
| 7,820,799 B2 | 10/2010 | Godavarti et al. |
| 7,834,158 B2 | 11/2010 | Hober |
| 7,834,162 B2 | 11/2010 | Zhou |
| 7,884,264 B2 | 2/2011 | Dickey et al. |
| 7,901,581 B2 | 3/2011 | Bryntesson et al. |
| 8,080,246 B2 | 12/2011 | Lin et al. |
| 8,084,032 B2 | 12/2011 | Yumioka et al. |
| 8,182,696 B2 | 5/2012 | Theoleyre et al. |
| 8,183,207 B2 | 5/2012 | Lin et al. |
| 8,198,404 B2 | 6/2012 | Hober |

(Continued)

FOREIGN PATENT DOCUMENTS

| EP | 2202310 A2 | 6/2010 |
|---|---|---|
| EP | 2557157 A1 | 2/2013 |

(Continued)

OTHER PUBLICATIONS

European Office Action for EP Application No. 17728070.8 mailed Feb. 9, 2021 (4 pages).
Minakuchi et al., "Remarkable Alkaline Stability of an Engineering Protein A as Immunoglobulin Affinity Ligand: C Doman having only one Amino Acid Substitution," Protein Science, 2013, 22:1230-1238.
Non-Final Office Action for U.S. Appl. No. 16/682,855, mailed Dec. 5, 2019, 14 pages.
Australian Office Examination Report No. 1 for AU Application No. 2015348641 mailed Dec. 17, 2019, 12 pages.
Office Action received for GB Patent Application No. 1608232.3 mailed Mar. 1, 2017, 10 pages.

(Continued)

*Primary Examiner* — Maury A Audet
(74) *Attorney, Agent, or Firm* — Eversheds-Sutherland (US) LLP

(57) ABSTRACT

An Fc-binding polypeptide of improved alkali stability, comprising a mutant of an Fc-binding domain of *Staphylococcus* Protein A (SpA), as defined by SEQ ID NO: 1, SEQ ID NO: 2, SEQ ID NO:3, SEQ ID NO: 4, SEQ ID NO: 5, SEQ ID NO:6, SEQ ID NO:7, SEQ ID NO:8, SEQ ID NO 26 or SEQ ID NO 27, wherein at least the alanine residue at the position corresponding to position 42 in SEQ ID NO:4-7 has been mutated to arginine and/or wherein at least the aspartic acid residue at the position corresponding to position 37 in SEQ ID NO:4-7 has been mutated to glutamic acid.

13 Claims, 1 Drawing Sheet

Specification includes a Sequence Listing.

(56) References Cited

U.S. PATENT DOCUMENTS

| | | | |
|---|---|---|---|
| 8,263,750 B2 | 9/2012 | Shukla et al. |
| 8,282,914 B2 | 10/2012 | Chou et al. |
| 8,329,660 B2 | 12/2012 | Hall et al. |
| 8,329,860 B2 | 12/2012 | Hall et al. |
| 8,354,510 B2 | 1/2013 | Hober et al. |
| 8,377,448 B2 | 2/2013 | Smith et al. |
| 8,586,713 B2 | 11/2013 | Davis et al. |
| 8,592,555 B2 | 11/2013 | Spector |
| 8,617,881 B2 | 12/2013 | Coljee et al. |
| 8,674,073 B2 | 3/2014 | Majima et al. |
| 8,728,479 B2 | 5/2014 | Greene et al. |
| 8,754,196 B2 | 6/2014 | Spector |
| 8,772,447 B2 | 7/2014 | Hall et al. |
| 8,822,642 B2 | 9/2014 | Levin et al. |
| 8,853,371 B2 | 10/2014 | Alfonso et al. |
| 8,859,726 B2 | 10/2014 | Bjorkman et al. |
| 8,883,134 B2 | 11/2014 | Cho et al. |
| 8,895,706 B2 | 11/2014 | Spector et al. |
| 9,018,305 B2 | 4/2015 | Spector et al. |
| 9,024,000 B2 | 5/2015 | Jeon et al. |
| 9,040,661 B2 | 5/2015 | Nakamura et al. |
| 9,051,375 B2 | 6/2015 | Li et al. |
| 9,073,970 B2 | 7/2015 | Muller-Spath et al. |
| 9,149,738 B2 | 10/2015 | Skudas |
| 9,156,892 B2 | 10/2015 | Hober |
| 9,162,161 B2 | 10/2015 | Tamori et al. |
| 9,187,555 B2 | 11/2015 | Bjorkman et al. |
| 9,266,939 B2 | 2/2016 | Crine et al. |
| 9,284,347 B2 | 3/2016 | Eckermann et al. |
| 9,290,549 B2 | 3/2016 | Hall et al. |
| 9,290,573 B2 | 3/2016 | Cong et al. |
| 9,296,791 B2 | 3/2016 | Hober et al. |
| 9,382,305 B2 | 7/2016 | Wilmen et al. |
| 9,481,730 B2 | 11/2016 | Bruenker et al. |
| 9,493,529 B2 | 11/2016 | Blanche et al. |
| 9,499,608 B2 | 11/2016 | Chen et al. |
| 9,517,264 B2 | 12/2016 | Fachini et al. |
| 9,534,023 B2 | 1/2017 | Hober |
| 9,540,442 B2 | 1/2017 | Tsurushita et al. |
| 9,556,258 B2 | 1/2017 | Nti-Gyabaah et al. |
| 9,573,989 B2 | 2/2017 | Watzig et al. |
| 9,587,235 B2 | 3/2017 | Buechler et al. |
| 9,637,541 B2 | 5/2017 | Kim et al. |
| 9,637,557 B2 | 5/2017 | Scheer et al. |
| 9,650,442 B2 | 5/2017 | Hosse et al. |
| 9,662,373 B2 | 5/2017 | Cload et al. |
| 9,676,871 B2 | 6/2017 | Strop et al. |
| 9,688,978 B2 | 6/2017 | Buechler et al. |
| 9,695,233 B2 | 7/2017 | Duerr et al. |
| 9,708,405 B2 | 7/2017 | Liu et al. |
| 9,714,292 B2 | 7/2017 | Auer et al. |
| 9,920,098 B2 | 3/2018 | Yoshida et al. |
| 10,065,995 B2 | 9/2018 | Yoshida et al. |
| 10,501,557 B2 * | 12/2019 | Rodrigo ............ C07K 16/46 |
| 10,513,537 B2 | 12/2019 | Rodrigo et al. |
| 10,654,887 B2 | 5/2020 | Rodrigo et al. |
| 10,703,774 B2 | 7/2020 | Forss et al. |
| 10,711,035 B2 | 7/2020 | Rodrigo et al. |
| 10,730,908 B2 | 8/2020 | Forss et al. |
| 10,808,042 B2 | 10/2020 | Haupts |
| 10,889,615 B2 | 1/2021 | Rodrigo |
| 10,918,971 B2 | 2/2021 | Hober |
| 10,995,113 B2 | 5/2021 | Rodrigo et al. |
| 11,136,359 B2 | 10/2021 | Rodrigo et al. |
| 11,566,082 B2 * | 1/2023 | Rodrigo ............ C07K 14/31 |
| 11,623,941 B2 | 4/2023 | Forss |
| 11,685,764 B2 | 6/2023 | Rodrigo |
| 2005/0097625 A1 | 5/2005 | Meade et al. |
| 2005/0143566 A1 | 6/2005 | Hober |
| 2006/0194955 A1 | 8/2006 | Hober et al. |
| 2007/0207500 A1 | 9/2007 | Bian et al. |
| 2008/0167450 A1 | 7/2008 | Pan |
| 2008/0230478 A1 | 9/2008 | Johansson et al. |
| 2010/0221844 A1 | 9/2010 | Bian et al. |
| 2010/0256338 A1 | 10/2010 | Brinkmann et al. |
| 2010/0267932 A1 | 10/2010 | Eon-Duval et al. |
| 2011/0117605 A1 | 5/2011 | Tolstrup et al. |
| 2011/0144311 A1 | 6/2011 | Chmielowski et al. |
| 2012/0071637 A1 | 3/2012 | Ambrosius et al. |
| 2012/0091063 A1 | 4/2012 | Bangtsson et al. |
| 2012/0148390 A1 | 6/2012 | Johansson et al. |
| 2012/0149875 A1 | 6/2012 | Hsu et al. |
| 2012/0208234 A1 | 8/2012 | Yoshida et al. |
| 2012/0238730 A1 | 9/2012 | Dong et al. |
| 2012/0263722 A1 | 10/2012 | Ghayur et al. |
| 2012/0283416 A1 | 11/2012 | Frauenschuh et al. |
| 2013/0096276 A1 | 4/2013 | Yoshida et al. |
| 2013/0096284 A1 | 4/2013 | Ishihara |
| 2013/0197197 A1 | 8/2013 | Eckermann et al. |
| 2013/0274451 A1 | 10/2013 | Bjorkman et al. |
| 2014/0018525 A1 | 1/2014 | Goklen et al. |
| 2014/0031522 A1 | 1/2014 | Li et al. |
| 2014/0094593 A1 | 4/2014 | Frauenschuh |
| 2014/0100356 A1 | 4/2014 | Yoshida et al. |
| 2014/0107315 A1 * | 4/2014 | Yoshida ............ C07K 14/31 435/252.35 |
| 2014/0148390 A1 | 5/2014 | Haupts et al. |
| 2014/0154270 A1 | 6/2014 | Wang et al. |
| 2014/0155565 A1 | 6/2014 | Joehnck et al. |
| 2014/0228548 A1 | 8/2014 | Galperina |
| 2014/0242624 A1 | 8/2014 | Valliere-Douglass et al. |
| 2014/0251911 A1 | 9/2014 | Skudas |
| 2014/0303356 A1 | 10/2014 | Gramer et al. |
| 2014/0329995 A1 | 11/2014 | Johansson et al. |
| 2015/0009380 A1 | 1/2015 | Kobayashi et al. |
| 2015/0044209 A1 | 2/2015 | Brodt et al. |
| 2015/0080554 A1 | 3/2015 | Ander et al. |
| 2015/0093800 A1 | 4/2015 | Mahajan et al. |
| 2015/0133636 A1 | 5/2015 | Xenopoulos et al. |
| 2015/0140683 A1 | 5/2015 | Rueger et al. |
| 2015/0209445 A1 | 7/2015 | Maderna et al. |
| 2015/0210749 A1 | 7/2015 | Combs et al. |
| 2015/0218250 A1 | 8/2015 | Auer et al. |
| 2015/0368352 A1 | 12/2015 | Liu |
| 2016/0024147 A1 | 1/2016 | Tustian et al. |
| 2016/0053025 A1 | 2/2016 | Oh et al. |
| 2016/0083480 A1 | 3/2016 | Ng et al. |
| 2016/0090426 A1 | 3/2016 | Zhou et al. |
| 2016/0108084 A1 | 4/2016 | Gruber et al. |
| 2016/0145340 A1 | 5/2016 | Borges et al. |
| 2016/0152668 A1 | 6/2016 | Hober |
| 2016/0152725 A1 | 6/2016 | Cheung et al. |
| 2016/0158377 A1 | 6/2016 | Ackler et al. |
| 2016/0159855 A1 | 6/2016 | Rodrigo et al. |
| 2016/0159857 A1 | 6/2016 | Rodrigo et al. |
| 2016/0159929 A1 | 6/2016 | Lee et al. |
| 2016/0166634 A1 | 6/2016 | Caplan et al. |
| 2016/0200797 A1 | 7/2016 | Hall et al. |
| 2016/0237124 A1 | 8/2016 | Qian et al. |
| 2016/0251395 A1 | 9/2016 | Davis et al. |
| 2016/0272710 A1 | 9/2016 | Hilden et al. |
| 2016/0289335 A1 | 10/2016 | Weisser et al. |
| 2016/0296648 A1 | 10/2016 | Chevallier et al. |
| 2016/0304617 A1 | 10/2016 | Damle et al. |
| 2016/0310612 A1 | 10/2016 | Lyon et al. |
| 2016/0311853 A1 | 10/2016 | Geierstanger et al. |
| 2016/0340443 A1 | 11/2016 | Rossi et al. |
| 2016/0362474 A1 | 12/2016 | Wang et al. |
| 2016/0362500 A1 | 12/2016 | Knoetgen |
| 2017/0043033 A1 | 2/2017 | Strop et al. |
| 2017/0081412 A1 | 3/2017 | Newman et al. |
| 2017/0088596 A1 | 3/2017 | Scheer et al. |
| 2017/0096485 A1 | 4/2017 | Bacac et al. |
| 2017/0114141 A1 | 4/2017 | Amann et al. |
| 2017/0121282 A1 | 5/2017 | Geierstanger et al. |
| 2017/0152298 A1 | 6/2017 | Banerjee et al. |
| 2017/0165370 A1 | 6/2017 | Govindan et al. |
| 2017/0182179 A1 | 6/2017 | Ackler et al. |
| 2017/0204199 A1 | 7/2017 | Sanches et al. |
| 2017/0216452 A1 | 8/2017 | Ma et al. |
| 2017/0218051 A1 | 8/2017 | Gnauer et al. |
| 2017/0226172 A1 | 8/2017 | Mohammadi et al. |
| 2017/0233453 A1 | 8/2017 | Zheng et al. |
| 2017/0233490 A1 | 8/2017 | Bossenmaier et al. |

(56) References Cited

U.S. PATENT DOCUMENTS

| | | | |
|---|---|---|---|
| 2017/0247417 | A1 | 8/2017 | Chang et al. |
| 2017/0247467 | A1 | 8/2017 | Amann et al. |
| 2017/0260265 | A1 | 9/2017 | Duerr et al. |
| 2017/0260289 | A1 | 9/2017 | Petersen et al. |
| 2017/0327534 | A1 | 11/2017 | Rodrigo et al. |
| 2017/0334954 | A1 | 11/2017 | Rodrigo et al. |
| 2019/0119318 | A1 | 4/2019 | Rodrigo et al. |
| 2021/0147577 | A1* | 5/2021 | Rodrigo ............. B01J 20/289 |

FOREIGN PATENT DOCUMENTS

| | | | |
|---|---|---|---|
| EP | 2202310 | B1 | 3/2013 |
| EP | 2728000 | A1 | 5/2014 |
| EP | 3050902 | A1 | 8/2016 |
| EP | 2412809 | B1 | 8/2017 |
| EP | 3335789 | A1 | 6/2018 |
| EP | 2728000 | B1 | 12/2018 |
| IN | 201717016314 | A | 10/2017 |
| JP | 2500329 | B2 | 5/1996 |
| JP | 2000-500649 | A | 1/2000 |
| JP | 2006304633 | A | 11/2006 |
| JP | 2010-081866 | A | 4/2010 |
| JP | 2016-079149 | A | 5/2016 |
| JP | 2016-079153 | A | 5/2016 |
| JP | 2017-037070 | A | 2/2017 |
| JP | 2017-525397 | A | 9/2017 |
| WO | 88/09344 | A1 | 12/1998 |
| WO | 03/080655 | A1 | 10/2003 |
| WO | 2005/075507 | A1 | 8/2005 |
| WO | 2008/049106 | A2 | 4/2008 |
| WO | 2011107518 | A1 | 9/2011 |
| WO | 2011118699 | A1 | 9/2011 |
| WO | 2012/087231 | A1 | 6/2012 |
| WO | 2012074463 | A1 | 6/2012 |
| WO | 2012083425 | A1 | 6/2012 |
| WO | 2012086660 | A1 | 6/2012 |
| WO | 2012/133349 | A1 | 10/2012 |
| WO | 2013/033517 | A1 | 3/2013 |
| WO | 2013/075849 | A1 | 5/2013 |
| WO | 2013/081540 | A1 | 6/2013 |
| WO | 2013/109302 | A2 | 7/2013 |
| WO | 2013/147691 | A1 | 10/2013 |
| WO | 2014046278 | A1 | 3/2014 |
| WO | 2014/159064 | A1 | 10/2014 |
| WO | 2014/186350 | A1 | 11/2014 |
| WO | 2014/192877 | A1 | 12/2014 |
| WO | 2015/005859 | A1 | 1/2015 |
| WO | 2015005862 | A1 | 1/2015 |
| WO | 2015/048330 | A2 | 4/2015 |
| WO | 2015046473 | A1 | 4/2015 |
| WO | 2015/166072 | A1 | 11/2015 |
| WO | 2016/030791 | A1 | 3/2016 |
| WO | 2016079033 | A1 | 5/2016 |
| WO | 2016079034 | A1 | 5/2016 |
| WO | 2016/097300 | A1 | 6/2016 |
| WO | 2017/011342 | A1 | 1/2017 |
| WO | 2017/036805 | A1 | 3/2017 |
| WO | 2017/050889 | A1 | 3/2017 |
| WO | 2017194592 | A1 | 11/2017 |
| WO | 2017194594 | A1 | 11/2017 |

OTHER PUBLICATIONS

Gulich et al., "Stability towards alkaline conditions can be engineered into a protein ligand", Journal of Biotechnology, vol. 80, 2000, pp. 169-178.

International Search Report for PCT Application No. PCT/EP2017/061164, mailed Aug. 30, 2017, 5 pages.

International Search Report and Written Opinion received for PCT Application No. PCT/EP2017/061158, mailed Jul. 13, 2017, 15 pages.

PCT International Search Report and Written Opinion for PCT Application No. PCT/EP2017/061164, mailed Sep. 5, 2017 (10 pages).

Uhlen et al., "Complete Sequence of the Staphylococccal Gene Encoding Protein A", Journal of Biological Chemistry, vol. 259, No. 3, Feb. 10, 1964, pp. 1695-1702.

Hedhammar et al., "Protein Engineering Strategies for Selective Protein Purification", Chemical Engineering Technology, vol. 28, No. 11, 2005, pp. 1315-1325.

Altshul et al., "Basic Local Alignment Search Tool", Journal of Molecular Biology, vol. 215, 1990, pp. 403-410.

U.S. Appl. No. 15/367,640, filed Dec. 2, 2016, 52 pages.

GB Search Report for GB Application No. 1608229.9 mailed Feb. 28, 2017 (10 pages).

Arshady, "Styrene Based Polymer Supports Developed by Suspension Polymerization", Chimica e L'Industria, 1988, 70(9):7-75.

Hjerten, "The Preparation of Agarose Spheres for Chromatography of Molecules and Particles", Biochim. Boiphys. Acta, 1964, 79:L393-398.

Gel Filtration Principles and Methods, Pharmacia LKB Biotechnology 1991, pp. 6-13.

JP Office Action for JP Application No. 2017-525398 mailed Nov. 11, 2019 (8 pages, English translation).

PCT International Search Report and Written Opinion for PCT Application No. PCT/EP2017/061162 mailed Sep. 11, 2017 (24 pages).

International Search Report for PCT Application No. PCT/EP2017/061160, mailed Aug. 25, 2017, 5 pages.

Bach et al., "Differential binding of heavy chain variable domain 3 antigen binding fragments to protein a chromatography resins," J Chromatography A, 2015, 1409: 60-69.

O'Seaghdha et al., "*Staphylococcus aureus* protein A binding to von Villebrand fator A1 domain is mediated by conserved IgG binding resins," FEBS J, 2006, 273, pp. 4831-4841.

Pakiman et al., "Comparison of Binding Capacity and Affinity of Monoclonal Antibody towards Different Affinity Resins using High-Throughput Chromatography Method," J Appl Sci, 2012, 12, 11, pp. 1136-1141.

Weidle et al., "The intriguing options of multispecific antibody formats for treatment of cancer," Cancer Genom. Proteom, 2013, 10, pp. 1-18.

International Search Report for PCT Application No. PCT/EP2015/076639, mailed Feb. 10, 2016 (12 pages).

International-type Search Report for ITS/SE2014/000256, mailed May 13, 2015 (5 pages).

International Search Report and Written Opinion for PCT/EP2017/061159, mailed Aug. 1, 2017 (14 pages).

Non-Final Office Action for U.S. Appl. No. 16/893,574 mailed Oct. 6, 2020 (39 pages).

Chinese Office Action for CN Application No. 201580062121.1 mailed Jun. 23, 2020 (39 pages, with English translation).

Japanese Office Action for Japanese Application No. 2017-525398, mailed Nov. 19, 2019 (8 pages).

European Office Action for EP Application No. 17728070.8 mailed Jul. 18, 2019 (9 pages).

Hober et al., "Protein A Chromatography for Antibody Purification," Journal of Chromatography B, 2007, 848:40-47.

European Office Action for EP Application No. 15797942.8 mailed Jun. 25, 2019 (4 pages).

Russian Office Action for RU Application No. 2017115345/10 mailed Apr. 2, 2019 (English translation, 19 pages).

Berry et al., "Substitution of Cysteine for Selenocysteine in Type 1 Iodothyronine Deiodinase Reduces the Catalytic Efficiency of the Protein but Enhances its Translation," Endocrinology, 1992, 131 ( 4 ): 1848-1852.

Gasser et al., "Antibody Production with Yeasts and Filamentous Fungi: On the Road to Large Scale?," Biotechnol Lett, 2007, 29:201-212.

Nikolaeva et al., "New Approach for Determination of the Identity of the Combined Vaccines for Diphtheria, Tetanus and Pertussis Prophylaxis," The Siberian Medical Journal, 2011, 26(2), 6 pages.

Pakula et al., "Genetic Analysis of Protein Stability and Function," Annu. Rev. Genet., 1989, 23:289-310.

(56) References Cited

OTHER PUBLICATIONS

Singapore Written Opinion and Search Report for SG Application No. 11201703035 3P mailed May 3, 2018 (11 pages).
PCT International Search Report and Written Opinion for PCT Application No. PCT/EP2015/076642 mailed Apr. 20, 2016 (19 pages).
Bostrom et al., "Purification Systems Based on Bacterial Surface Proteins," Protein Purification, 2012, Intech (49 pages).
Office Action Issued in Japanese Patent Application No. 2020-534551, mailed Dec. 5, 2022 with English Summary (13 Pages).
Japanese Office Action for JP Application No. 2018-558405 mailed Mar. 29, 2021 (12 pages with English translation).
"Use of Sodium Hydroxide for Cleaning and Sanitization of Chromatography Media and systems," Application Note 18-1124-57 AI, 2014, https://www.cytivalifesciences.co.jp/catalog/pdf/18112457AI_AppNote_NaOHforCIP_SIP_final_1.pdf.
Japanese Office Action for JP Application No. 2020-121312 mailed Aug. 10, 2021 (13 pages, with English translation).
Bostrom, T. et al., "Purification Systems Based on Bacterial Surface Proteins", Protein Purification, 2012, ISBN: 978-953-307-831-1, 89-136.
Japanese Office Action for JP Application No. 2018-558395 mailed May 24, 2021 (11 pages, with English Translation).
Indian Office Action for IN Application No. 201847041236 mailed Sep. 1, 2022 (7 pages).
Bowie, J., et al. "Deciphering the Message in Protein Sequences: Tolerance to Amino Acid Substitutions", Science, 1990, 247:4948, pp. 1306-1310.
Burgess, W.H., et al. "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", The Journal of Cell Biology, 1990, 111, pp. 2129-2138.
Lazar, E., et al. "Transforming Growth Factor ex: Mutation of Aspartic Acid 47 and Leucine 48 Results in Different Biological Activities", Molecular and Cellular Biology, 1988, 8(3): 1247-1252.
NIPA, CN, "First Office Action" App. No. 201780028976.1, mailed Sep. 3, 2021, 21 pages.
Mccaw et al. "Evaluation of a novel methacrylate-based protein A resin for the purificaiton of immunoglobulins and Fc-Fusion Proteins" Biotechnology Prog. 2014, 30(5) (Year: 2014), 12 pages.
Order Granted Request for Ex Parte Reexamination in U.S. Appl. No. 90/015,234, mailed Jun. 23, 2023, 11 pages.
Liu et al., mAbs 2:5. pp. 480-499. Sep./Oct. 2010 (Year: 2010).
Hahn et al. J. Chromatography A (2006) 11102:224-231 (Year: 2006) (abstract).
Japanese Office Action of JP Application No. 2022-007919, dated Jan. 30, 2023 (3 pages).
U.S. Non-Final Office Action from corresponding U.S. Appl. No. 17/114,773, mailed Jul. 6, 2023, 10 pages.
U.S. Non-Final Office Action from corresponding U.S. Appl. No. 18/298,857, mailed Mar. 12, 2024, 12 pages.

\* cited by examiner

Alignment of Fc-binding domains

| | | | | | | | |
|---|---|---|---|---|---|---|---|
| E    | -------AQQ | NAFYQVLNMP | NLNADQRNGF | IQSLKDDPSQ | SANVLGEAQK | LNDSQAPK | 51 | (SEQ ID NO: 1) |
| D    | ADAQQNKFNKDQQ | SAFYEILNMP | NLNEEQRNGF | IQSLKDDPSQ | STNVLGEAKK | LNESQAPK | 61 | (SEQ ID NO: 2) |
| A    | -ADNN-FNKEQQ | NAFYEILNMP | NLNEEQRNGF | IQSLKDDPSQ | SANLLAEAKK | LNESQAPK | 58 | (SEQ ID NO: 3) |
| B    | ---ADNKFNKEQQ | NAFYEILHLP | NLNEEQRNGF | IQSLKDDPSQ | SANLLAEAKK | LNDAQAPK | 58 | (SEQ ID NO: 4) |
| C    | ---ADNKFNKEQQ | NAFYEILHLP | NLTEEQRNGF | IQSLKDDPSV | SKEILAEAKK | LNDAQAPK | 58 | (SEQ ID NO: 5) |
| Z    | ---VDNKFNKEQQ | NAFYEILHLP | NLNEEQRNAF | IQSLKDDPSQ | SANLLAEAKK | LNDAQAPK | 58 | (SEQ ID NO: 6) |
| Zvar | ---VDAKFDKEQQ | NAFYEILHLP | NLTEEQRNAF | IQSLKDDPSQ | SANLLAEAKK | LNDAQAPK | 58 | (SEQ ID NO: 7) |
|      | ------KEQQ | NAFYEILHLP | NLTEEQRNAF | IQSLKDDPSQ | SANLLAEAKK | LNDAQAPK | 52 | (SEQ ID NO: 26) |
|      | ------KEQQ | NAFYEILHLP | NLTEEQRNGF | IQSLKDDPSV | SKEILAEAKK | LNDAQAPK | 52 | (SEQ ID NO: 27) |
| Pos  | 1 | 10 | 20 | 30 | 40 | 50 | 58 | |

MUTATED IMMUNOGLOBULIN-BINDING POLYPEPTIDES

CROSS REFERENCE TO RELATED APPLICATIONS

This application is a continuation of U.S. application Ser. No. 15/525,688 filed on May 10, 2017, which claims the priority benefit of PCT/EP2015/076642 filed on Nov. 16, 2015 which claims priority benefit of Swedish Application No. 1451376-6 filed Nov. 17, 2014 and Great Britain Application Nos. 1510261.9 and 1510263.5 filed Jun. 12, 2015 and Jun. 12, 2015, respectively. The entire contents of which are hereby incorporated by reference herein.

SEQUENCE LISTING

The instant application contains a Sequence Listing which has been submitted electronically in ASCII format and is hereby incorporated by reference in its entirety. Said ASCII copy, created on May 2, 2017, is named 3911473_1.txt and is 24,536 bytes in size.

TECHNICAL FIELD OF THE INVENTION

The present invention relates to the field of affinity chromatography, and more specifically to mutated immunoglobulin-binding domains of Protein A, which are useful in affinity chromatography of immunoglobulins. The invention also relates to multimers of the mutated domains and to separation matrices containing the mutated domains or multimers.

BACKGROUND OF THE INVENTION

Immunoglobulins represent the most prevalent biopharmaceutical products in either manufacture or development worldwide. The high commercial demand for and hence value of this particular therapeutic market has led to the emphasis being placed on pharmaceutical companies to maximize the productivity of their respective mAb manufacturing processes whilst controlling the associated costs.

Affinity chromatography is used in most cases, as one of the key steps in the purification of these immunoglobulin molecules, such as monoclonal or polyclonal antibodies. A particularly interesting class of affinity reagents is proteins capable of specific binding to invariable parts of an immunoglobulin molecule, such interaction being independent on the antigen-binding specificity of the antibody. Such reagents can be widely used for affinity chromatography recovery of immunoglobulins from different samples such as but not limited to serum or plasma preparations or cell culture derived feed stocks. An example of such a protein is staphylococcal protein A, containing domains capable of binding to the Fc and Fab portions of IgG immunoglobulins from different species.

Staphylococcal protein A (SpA) based reagents have due to their high affinity and selectivity found a widespread use in the field of biotechnology, e.g. in affinity chromatography for capture and purification of antibodies as well as for detection or quantification. At present, SpA-based affinity medium probably is the most widely used affinity medium for isolation of monoclonal antibodies and their fragments from different samples including industrial cell culture supernatants. Accordingly, various matrices comprising protein A-ligands are commercially available, for example, in the form of native protein A (e.g. Protein A SEPHAROSE™, GE Healthcare, Uppsala, Sweden) and also comprised of recombinant protein A (e.g. rProtein A-SEPHAROSE™, GE Healthcare). More specifically, the genetic manipulation performed in the commercial recombinant protein A product is aimed at facilitating the attachment thereof to a support and at increasing the productivity of the ligand.

These applications, like other affinity chromatography applications, require comprehensive attention to definite removal of contaminants. Such contaminants can for example be non-eluted molecules adsorbed to the stationary phase or matrix in a chromatographic procedure, such as non-desired biomolecules or microorganisms, including for example proteins, carbohydrates, lipids, bacteria and viruses. The removal of such contaminants from the matrix is usually performed after a first elution of the desired product in order to regenerate the matrix before subsequent use. Such removal usually involves a procedure known as cleaning-in-place (CIP), wherein agents capable of eluting contaminants from the stationary phase are used. One such class of agents often used is alkaline solutions that are passed over said stationary phase. At present the most extensively used cleaning and sanitizing agent is NaOH, and the concentration thereof can range from 0.1 up to e.g. 1 M, depending on the degree and nature of contamination. This strategy is associated with exposing the matrix to solutions with pH-values above 13. For many affinity chromatography matrices containing proteinaceous affinity ligands such alkaline environment is a very harsh condition and consequently results in decreased capacities owing to instability of the ligand to the high pH involved.

An extensive research has therefore been focused on the development of engineered protein ligands that exhibit an improved capacity to withstand alkaline pH-values. For example, Gülich et al. (Susanne Gülich, Martin Linhult, Per-Åke Nygren, Mathias Uhlén, Sophia Hober, Journal of Biotechnology 80 (2000), 169-178) suggested protein engineering to improve the stability properties of a Streptococcal albumin-binding domain (ABD) in alkaline environments. Gülich et al. created a mutant of ABD, wherein all the four asparagine residues have been replaced by leucine (one residue), aspartate (two residues) and lysine (one residue). Further, Gülich et al. report that their mutant exhibits a target protein binding behavior similar to that of the native protein, and that affinity columns containing the engineered ligand show higher binding capacities after repeated exposure to alkaline conditions than columns prepared using the parental non-engineered ligand. Thus, it is concluded therein that all four asparagine residues can be replaced without any significant effect on structure and function.

Recent work shows that changes can also be made to protein A (SpA) to effect similar properties. US patent application publication US 2005/0143566, which is hereby incorporated by reference in its entirety, discloses that when at least one asparagine residue is mutated to an amino acid other than glutamine or aspartic acid, the mutation confers an increased chemical stability at pH-values of up to about 13-14 compared to the parental SpA, such as the B-domain of SpA, or Protein Z, a synthetic construct derived from the B-domain of SpA (U.S. Pat. No. 5,143,844, incorporated by reference in its entirety). The authors show that when these mutated proteins are used as affinity ligands, the separation media as expected can better withstand cleaning procedures using alkaline agents. Further mutations of protein A domains with the purpose of increasing the alkali stability have also been published in WO 2008/039141, JP 2006304633A, EP 1992692A1, EP2202310A2, WO 2010/110288, WO 2012/086660, WO 2012/083425, WO2012/

087230 and WO2014/146350, all of which are incorporated by reference in their entireties. However, the currently available mutations are still sensitive to alkaline pH and the NaOH concentration during cleaning is usually limited to 0.1 M, which means that complete cleaning is difficult to achieve. Higher NaOH concentrations, which would improve the cleaning, lead to unacceptable capacity losses.

There is thus still a need in this field to obtain a separation matrix containing protein ligands having a further improved stability towards alkaline cleaning procedures.

SUMMARY OF THE INVENTION

One aspect of the invention is to provide a polypeptide with improved alkaline stability. This is achieved with a polypeptide as defined in claim 1.

One advantage is that the alkaline stability is improved over the parental polypeptides, with a maintained highly selective binding towards immunoglobulins and other Fc-containing proteins.

A second aspect of the invention is to provide a multimer with improved alkaline stability, comprising a plurality of polypeptides. This is achieved with a multimer as defined in the claims.

A third aspect of the invention is to provide a nucleic acid or a vector encoding a polypeptide or multimer with improved alkaline stability. This is achieved with a nucleic acid or vector as defined in the claims.

A fourth aspect of the invention is to provide an expression system capable of expressing a polypeptide or multimer with improved alkaline stability. This is achieved with an expression system as defined in the claims.

A fifth aspect of the invention is to provide a separation matrix capable of selectively binding immunoglobulins and other Fc-containing proteins and exhibiting an improved alkaline stability. This is achieved with a separation matrix as defined in the claims.

A sixth aspect of the invention is to provide an efficient and economical method of isolating an immunoglobulin or other Fc-containing protein. This is achieved with a method as defined in the claims.

Further suitable embodiments of the invention are described in the dependent claims.

DEFINITIONS

The terms "antibody" and "immunoglobulin" are used interchangeably herein, and are understood to include also fragments of antibodies, fusion proteins comprising antibodies or antibody fragments and conjugates comprising antibodies or antibody fragments.

The terms an "Fc-binding polypeptide" and "Fc-binding protein" mean a polypeptide or protein respectively, capable of binding to the crystallisable part (Fc) of an antibody and includes e.g. Protein A and Protein G, or any fragment or fusion protein thereof that has maintained said binding property.

The term "linker" herein means an element linking two polypeptide units monomers or domains to each other in a multimer.

The term "spacer" herein means an element connecting a polypeptide or a polypeptide multimer to a support.

BRIEF DESCRIPTION OF FIGURES

FIG. 1 shows an alignment of the Fc-binding domains as defined by SEQ ID NO:1-7 and 26-27.

DETAILED DESCRIPTION OF EMBODIMENTS

In one aspect the present invention discloses an Fc-binding polypeptide, which comprises, or consists essentially of, a mutant of an Fc-binding domain of *Staphylococcus* Protein A (SpA), as defined by, or having at least 90%, at least 95% or at least 98% identity to, SEQ ID NO: 1 (E-domain), SEQ ID NO: 2 (D-domain), SEQ ID NO:3 (A-domain), SEQ ID NO: 4 (B-domain), SEQ ID NO: 5 (C-domain), SEQ ID NO:6 (Protein Z), SEQ ID NO:7 (Zvar) or SEQ ID NO:8 (variant A-domain), SEQ ID NO 26 (Zvar without the linker region amino acids 1-6) or SEQ ID NO 27 (C-domain without the linker region amino acids 1-6) as illustrated in FIG. 1, wherein at least the alanine residue at the position corresponding to position* 42 in SEQ ID NO:4-7 has been mutated to another amino acid residue, such as arginine, and/or wherein at least the aspartic acid residue at the position corresponding to position 37 in SEQ ID NO:4-7 has been mutated to glutamic acid. Protein Z (SEQ ID NO:6) is a mutated B-domain as disclosed in U.S. Pat. No. 5,143,844, while SEQ ID NO 7 denotes a further mutated variant of Protein Z, here called Zvar, with the mutations N3A,N6D,N23T. SEQ ID NO:8 is a natural variant of the A-domain in Protein A from *Staphylococcus aureus* strain N315, having an A46S mutation, using the position terminology of FIG. 1. The mutation of D37 and/or A42 in these domains confers an improved alkali stability in comparison with the parental domain/polypeptide, without impairing the immunoglobulin-binding properties. Hence, the polypeptide can also be described as an Fc- or immunoglobulin-binding polypeptide, or alternatively as an Fc- or immunoglobulin-binding polypeptide unit.

Throughout this description, the amino acid residue position numbering convention of FIG. 1 is used, and the position numbers are designated as corresponding to those in SEQ ID NO 4-7.

In alternative language, the invention discloses an Fc-binding polypeptide which comprises a sequence as defined by, or having at least 90%, at least 95% or at least 98% identity to SEQ ID NO 28.

SEQ ID NO 28

KEX$_1$Q X$_2$AFYEILX$_3$LP NLTEEQRX$_4$X$_5$F IQX$_6$LKDX$_7$PSX$_8$

SX$_9$X$_{10}$X$_{11}$LAEAKX$_{12}$X$_{13}$NDAQAPK where individually of each other X$_1$=A or Q X$_2$=E, K or N X$_3$=H or K X$_4$=A or N X$_5$=A or G X$_6$=S or K X$_7$=E or D X$_8$=Q or V X$_9$=K, R or A X$_{10}$=A, E or N X$_{11}$=I or L X$_{12}$=K or R X$_{13}$=L or Y The D37E (X$_7$) and/or A42R (X$_9$) mutations may be the only mutations or the polypeptide may also comprise further mutations, such as substitutions in at least one of the positions corresponding to positions 3, 6, 9, 10, 15, 18, 23, 28, 29, 32, 33, 36, 37, 40, 42, 43, 44, 47, 50, 51, 55 and 57 in SEQ ID NO:4-8. In one or more of these positions, the original amino acid residue may e.g. be substituted with an amino acid which is not asparagine, proline or cysteine. The original amino acid residue may e.g. be substituted with an alanine, a valine, a threonine, a serine, a lysine, a glutamic acid or an aspartic acid. Further, one or more amino acid residues may be deleted, e.g. from positions 1-6 and/or from positions 56-58.

In some embodiments, the amino acid residue at the position corresponding to position 9 in SEQ ID NO:4-7 ($X_1$) is an amino acid other than glutamine, asparagine, proline or cysteine, such as an alanine. In specific embodiments, in SEQ ID NO: 7 the amino acid residue at position 9 is an alanine and the amino acid residue at position 11 is a lysine. Mutations at position 9 are also discussed in copending application PCT/SE2014/050872, which is hereby incorporated by reference in its entirety.

In some embodiments, the amino acid residue at the position corresponding to position 50 in SEQ ID NO:4-7 ($X_{12}$) is an arginine or a glutamic acid.

In certain embodiments, the amino acid residue at the position corresponding to position 11 in SEQ ID NO:4-7 ($X_2$) is a lysine or a glutamic acid.

In certain embodiments, the amino acid residue at the position corresponding to position 3 in SEQ ID NO:4-7 is an alanine and/or the amino acid residue at the position corresponding to position 6 in SEQ ID NO:4-7 is an aspartic acid. One of the amino acid residues at positions 3 and 6 may be an asparagine and in an alternative embodiment both amino acid residues at positions 3 and 6 may be asparagines.

In some embodiments the amino acid residue at the position corresponding to position 43 in SEQ ID NO:4-7 ($X_{10}$) is an alanine or a glutamic acid, such as an alanine. In specific embodiments, the amino acid residue at position 9 in SEQ ID NO: 7 is alanine, the amino acid residue at position 11 is lysine or glutamic acid, while the amino acid residue at position 43 is alanine or glutamic acid.

In certain embodiments the amino acid residue residue at the position corresponding to position 28 in SEQ ID NO:4-7 (X4) is an alanine or an asparagine, such as an alanine.

In some embodiments the amino acid residue at the position corresponding to position 40 in SEQ ID NO:4-7 (X8) is selected from the group consisting of asparagine, alanine, glutamic acid and valine, or from the group consisting of glutamic acid and valine.

In certain embodiments, the amino acid residue at the position corresponding to position 42 in SEQ ID NO:4-7 (X9) is an alanine, lysine or arginine.

In some embodiments the amino acid residue at the position corresponding to position 18 in SEQ ID NO:4-7 (X3) is a lysine or a histidine, such as a lysine.

In certain embodiments the amino acid residue at the position corresponding to position 33 in SEQ ID NO:4-7 (X6) is a lysine or a serine, such as a lysine.

In some embodiments the amino acid residue at the position corresponding to position 37 in SEQ ID NO:4-7 (X7) is a glutamic acid or an aspartic acid, such as a glutamic acid.

In certain embodiments the amino acid residue at the position corresponding to position 51 in SEQ ID NO:4-7 (X13) is a tyrosine or a leucine, such as a tyrosine.

In some embodiments, the amino acid residue at the position corresponding to position 44 in SEQ ID NO:4-7 (X11) is a leucine or an isoleucine. In specific embodiments, the amino acid residues at positions 9 and 11 in SEQ ID NO: 7 are alanine and lysine respectively, while the amino acid residue at position 44 is isoleucine. Optionally, the amino acid residue at position 43 may then be alanine or glutamic acid.

In some embodiments, the amino acid residues at the positions corresponding to positions 1, 2, 3 and 4 or to positions 3, 4, 5 and 6 in SEQ ID NO: 4-7 have been deleted. In specific variants of these embodiments, the parental polypeptide is the C domain of Protein A (SEQ ID NO: 5). The effects of these deletions on the native C domain are described in U.S. Pat. Nos. 9,018,305 and 8,329,860, which are hereby incorporated by reference in their entireties.

In certain embodiments, the mutation in SEQ ID NO 4-7, such as in SEQ ID NO 7, is selected from the group consisting of: D37E; A42R; N11K, H18K, S33K, D37E, A42R, N43A, L44I, K50R, L51Y; Q9A, N11K, H18K, S33K, D37E, A42R, N43A, L44I, K50R, L51Y; N11K, H18K, D37E, A42R, N43A, L44I; Q9A, N11K, H18K, D37E, A42R, N43A, L44I; Q9A, N11K, H18K, D37E, A42R, N43A, L44I, K50R; Q9A, N11K, H18K, D37E, A42R; Q9A, N11E, D37E, Q40V, A42K, N43A, L44I and Q9A, N11E, D37E, Q40V, A42R, N43A, L44I. These mutations provide particularly high alkaline stabilities.

In some embodiments, the polypeptide comprises or consists essentially of a sequence selected from the group consisting of SEQ ID NO: 9-18 and 24-25; 10-18 and 24-25 or 11-18 and 24-25. The polypeptide may e.g. be defined by a sequence selected from the group above or from subsets of this group, but it may also comprise additional amino acid residues at the N- and/or C-terminal end, e.g. a leader sequence at the N-terminal end and/or a tail sequence at the C-terminal end.

```
Zvar(D37E)
                                              SEQ ID NO 9
VDAKFDKEQQ NAFYEILHLP NLTEEQRNAF IQSLKDEPSQ

SANLLAEAKK LNDAQAPK

Zvar(A42R)
                                              SEQ ID NO 10
VDAKFDKEQQ NAFYEILHLP NLTEEQRNAF IQSLKDDPSQ

SRNLLAEAKK LNDAQAPK

Zvar(S33K, D37E, A42R, N43A, L44I, K50R,L51Y)
                                              SEQ ID NO: 11
VDAKFDKEQQ NAFYEILHLP NLTEEQRNAF IQKLKDEPSQ

SRAILAEAKR YNDAQAPK

Zvar(H18K, S33K, D37E, A42R, N43A, L44I, K50R,
L51Y)
                                              SEQ ID NO: 12
VDAKFDKEQQ NAFYEILKLP NLTEEQRNAF IQKLKDEPSQ

SRAILAEAKR YNDAQAPK

Zvar(N11K, H18K, S33K, D37E, A42R, N43A, L44I,
K50R, L51Y)
                                              SEQ ID NO 13
VDAKFDKEQQ KAFYEILKLP NLTEEQRNAF IQKLKDEPSQ

SRAILAEAKR YNDAQAPK

Zvar(Q9A, N11K, H18K, S33K, D37E, A42R, N43A,
L44I, K50R, L51Y)
                                              SEQ ID NO 14
VDAKFDKEAQ KAFYEILKLP NLTEEQRAAF IQKLKDEPSQ

SRAILAEAKR YNDAQAPK

Zvar(N11K, H18K, D37E, A42R, N43A, L44I)
                                              SEQ ID NO 15
VDAKFDKEQQ KAFYEILKLP NLTEEQRNAF IQSLKDEPSQ

SRAILAEAKK LNDAQAPK
```

```
Zvar(Q9A, N11K, H18K, D37E, A42R, N43A, L44I)
                                              SEQ ID NO 16
VDAKFDKEAQ KAFYEILKLP NLTEEQRNAF IQSLKDEPSQ

SRAILAEAKK LNDAQAPK

Zvar(Q9A, N11K, H18K, D37E, A42R, N43A, L44I,
K50R)
                                              SEQ ID NO 17
VDAKFDKEAQ KAFYEILKLP NLTEEQRNAF IQSLKDEPSQ

SRAILAEAKR LNDAQAPK

Zvar(Q9A, N11K, H18K, D37E, A42R)
                                              SEQ ID NO 18
VDAKFDKEAQ KAFYEILKLP NLTEEQRNAF IQSLKDEPSQ

SRNLLAEAKK LNDAQAPK

Zvar(Q9A, N11E, D37E, Q40V, A42K, N43A, L44I)
                                              SEQ ID NO 24
VDAKFDKEAQ EAFYEILHLP NLTEEQRNAF IQSLKDEPSV

SKAILAEAKK LNDAQAPK

Zvar(Q9A, N11E, D37E, Q40V, A42R, N43A, L44I)
                                              SEQ ID NO 25
VDAKFDKEAQ EAFYEILHLP NLTEEQRNAF IQSLKDEPSV

SRAILAEAKK LNDAQAPK
```

In a second aspect the present invention discloses a multimer comprising, or consisting essentially of, a plurality of polypeptide units as defined by any embodiment disclosed above. The multimer can e.g. be a dimer, a trimer, a tetramer, a pentamer, a hexamer, a heptamer, an octamer or a nonamer. It can be a homomultimer, where all the units in the multimer are identical or it can be a heteromultimer, where at least one unit differs from the others. Advantageously, all the units in the multimer are alkali stable, such as by comprising the mutations disclosed above. The polypeptides can be linked to each other directly by peptide bonds between the C-terminal and N-terminal ends of the polypeptides. Alternatively, two or more units in the multimer can be linked by linkers comprising oligomeric or polymeric species, such as elements comprising up to 15 or 30 amino acids, such as 1-5, 1-10 or 5-10 amino acids. The nature of such a linker should preferably not destabilize the spatial conformation of the protein units. This can e.g. be achieved by avoiding the presence of proline in the linkers. Furthermore, said linker should preferably also be sufficiently stable in alkaline environments not to impair the properties of the mutated protein units. For this purpose, it is advantageous if the linkers do not contain asparagine. It can additionally be advantageous if the linkers do not contain glutamine. The multimer may further at the N-terminal end comprise a plurality of amino acid residues e.g. originating from the cloning process or constituting a residue from a cleaved off signaling sequence. The number of additional amino acid residues may e.g. be 15 or less, such as 10 or less or 5 or less. As a specific example, the multimer may comprise an AQ sequence at the N-terminal end.

In certain embodiments, the multimer may comprise, or consist essentially of, a sequence selected from the group consisting of: SEQ ID NO 20, SEQ ID NO 21, SEQ ID NO 22 and SEQ ID NO 23. These sequences are listed below and named as Parent(Mutations)n, where n is the number of monomer units in a multimer.

```
Zvar(N11K, H18K, S33K, D37E, A42R, N43A, L44I,
K50R, L51Y)4
                                              SEQ ID NO 20
AQGT VDAKFDKEQQ KAFYEILKLP NLTEEQRNAF IQKLKDEPSQ

SRAILAEAKR YNDAQAPK VDAKFDKEQQ KAFYEILKLP

NLTEEQRNAF IQKLKDEPSQ SRAILAEAKR YNDAQAPK

VDAKFDKEQQ KAFYEILKLP NLTEEQRNAF IQKLKDEPSQ

SRAILAEAKR YNDAQAPK VDAKFDKEQQ KAFYEILKLP

NLTEEQRNAF IQKLKDEPSQ SRAILAEAKR YNDAQAPKC

Zvar(Q9A, N11K, H18K, D37E, A42R)4
                                              SEQ ID NO 21
AQGT VDAKFDKEAQ KAFYEILKLP NLTEEQRNAF IQSLKDEPSQ

SRNLLAEAKK LNDAQAPK VDAKFDKEAQ KAFYEILKLP

NLTEEQRNAF IQSLKDEPSQ SRNLLAEAKK LNDAQAPK

VDAKFDKEAQ KAFYEILKLP NLTEEQRNAF IQSLKDEPSQ

SRNLLAEAKK LNDAQAPK VDAKFDKEAQ KAFYEILKLP

NLTEEQRNAF IQSLKDEPSQ SRNLLAEAKK LNDAQAPKC

Zvar(Q9A, N11E, D37E, Q40V, A42K, N43A, L44I)4
                                              SEQ ID NO 22
AQGT VDAKFDKEAQ EAFYEILHLP NLTEEQRNAF IQSLKDEPSV

SKAILAEAKK LNDAQAPK VDAKFDKEAQ EAFYEILHLP

NLTEEQRNAF IQSLKDEPSV SKAILAEAKK LNDAQAPK

VDAKFDKEAQ EAFYEILHLP NLTEEQRNAF IQSLKDEPSV

SKAILAEAKK LNDAQAPK VDAKFDKEAQ EAFYEILHLP

NLTEEQRNAF IQSLKDEPSV SKAILAEAKK LNDAQAPKC

Zvar(Q9A, N11E, D37E, Q40V, A42R, N43A, L44I)4
                                              SEQ ID NO 23
AQGT VDAKFDKEAQ EAFYEILHLP NLTEEQRNAF IQSLKDEPSV

SRAILAEAKK LNDAQAPK VDAKFDKEAQ EAFYEILHLP

NLTEEQRNAF IQSLKDEPSV SRAILAEAKK LNDAQAPK

VDAKFDKEAQ EAFYEILHLP NLTEEQRNAF IQSLKDEPSV

SRAILAEAKK LNDAQAPK VDAKFDKEAQ EAFYEILHLP

NLTEEQRNAF IQSLKDEPSV SRAILAEAKK LNDAQAPKC
```

In some embodiments, the polypeptide and/or multimer, as disclosed above, further comprises at the C-terminal or N-terminal end one or more coupling elements, selected from the group consisting of one or more cysteine residues, a plurality of lysine residues and a plurality of histidine residues. The coupling element(s) may also be located within 1-5 amino acid residues, such as within 1-3 or 1-2 amino acid residues from the C-terminal or N-terminal end. The coupling element may e.g. be a single cysteine at the C-terminal end. The coupling element(s) may be directly linked to the C- or N-terminal end, or it/they may be linked via a stretch (linker) comprising up to 15 amino acids, such as 1-5, 1-10 or 5-10 amino acids. This is the case in particular for mutations of SEQ ID NO 26 and 27 and for the SEQ ID NO 28 polypeptide, where specific examples of linkers can e.g. be VDAKFD or ADNKFN, such as VDAKFD. This stretch should preferably also be sufficiently stable in alkaline environments not to impair the properties of the mutated protein. For this purpose, it is advantageous if the stretch does not contain asparagine. It can additionally be advantageous if the stretch does not contain glutamine.

An advantage of having a C-terminal cysteine is that endpoint coupling of the protein can be achieved through reaction of the cysteine thiol with an electrophilic group on a support. This provides excellent mobility of the coupled protein which is important for the binding capacity.

The alkali stability of the polypeptide or multimer can be assessed by coupling it to an SPR chip, e.g. to Biacore CM5 sensor chips as described in the examples, using e.g. NHS- or maleimide coupling chemistries, and measuring the immunoglobulin-binding capacity of the chip, typically using polyclonal human IgG, before and after incubation in alkaline solutions at a specified temperature, e.g. 22+/−2° C. The incubation can e.g. be performed in 0.5 M NaOH for a number of 10 min cycles, such as 100, 200 or 300 cycles. The IgG capacity of the matrix after 100 10 min incubation cycles in 0.5 M NaOH at 22+/−2° C. can be at least 55, such as at least 60, at least 80 or at least 90% of the IgG capacity before the incubation. Alternatively, the remaining IgG capacity after 100 cycles for a particular mutant measured as above can be compared with the remaining IgG capacity for the parental polypeptide/multimer. In this case, the remaining IgG capacity for the mutant may be at least 105%, such as at least 110%, at least 125%, at least 150% or at least 200% of the parental polypeptide/multimer.

In a third aspect the present invention discloses a nucleic acid encoding a polypeptide or multimer according to any embodiment disclosed above. Thus, the invention encompasses all forms of the present nucleic acid sequence such as the RNA and the DNA encoding the polypeptide or multimer. The invention embraces a vector, such as a plasmid, which in addition to the coding sequence comprises the required signal sequences for expression of the polypeptide or multimer according the invention. In one embodiment, the vector comprises nucleic acid encoding a multimer according to the invention, wherein the separate nucleic acids encoding each unit may have homologous or heterologous DNA sequences.

In a fourth aspect the present invention discloses an expression system, which comprises, a nucleic acid or a vector as disclosed above. The expression system may e.g. be a gram-positive or gram-negative prokaryotic host cell system, e.g. *E. coli* or *Bacillus* sp. which has been modified to express the present polypeptide or multimer. In an alternative embodiment, the expression system is a eukaryotic host cell system, such as a yeast, e.g. *Pichia pastoris* or *Saccharomyces cerevisiae*, or mammalian cells, e.g. CHO cells.

In a fifth aspect, the present invention discloses a separation matrix, wherein a plurality of polypeptides or multimers according to any embodiment disclosed above have been coupled to a solid support. Such a matrix is useful for separation of immunoglobulins or other Fc-containing proteins and, due to the improved alkali stability of the polypeptides/multimers, the matrix will withstand highly alkaline conditions during cleaning, which is essential for long-term repeated use in a bioprocess separation setting. The alkali stability of the matrix can be assessed by measuring the immunoglobulin-binding capacity, typically using polyclonal human IgG, before and after incubation in alkaline solutions at a specified temperature, e.g. 22+/−2° C. The incubation can e.g. be performed in 0.5 M or 1.0 M NaOH for a number of 15 min cycles, such as 100, 200 or 300 cycles, corresponding to a total incubation time of 25, 50 or 75 h. The IgG capacity of the matrix after 96-100 15 min incubation cycles or a total incubation time of 24 or 25 h in 0.5 M NaOH at 22+/−2° C. can be at least 80, such as at least 85, at least 90 or at least 95% of the IgG capacity before the incubation. The capacity of the matrix after a total incubation time of 24 h in 1.0 M NaOH at 22+/−2° C. can be at least 70, such as at least 80 or at least 90% of the IgG capacity before the incubation.

As the skilled person will understand, the expressed polypeptide or multimer should be purified to an appropriate extent before being immobilized to a support. Such purification methods are well known in the field, and the immobilization of protein-based ligands to supports is easily carried out using standard methods. Suitable methods and supports will be discussed below in more detail.

The solid support of the matrix according to the invention can be of any suitable well-known kind. A conventional affinity separation matrix is often of organic nature and based on polymers that expose a hydrophilic surface to the aqueous media used, i.e. expose hydroxy (—OH), carboxy (—COOH), carboxamido (—CONH$_2$, possibly in N-substituted forms), amino (—NH$_2$, possibly in substituted form), oligo- or polyethylenoxy groups on their external and, if present, also on internal surfaces. The solid support can suitably be porous. The porosity can be expressed as a Kav or Kd value (the fraction of the pore volume available to a probe molecule of a particular size) measured by inverse size exclusion chromatography, e.g. according to the methods described in Gel Filtration Principles and Methods, Pharmacia LKB Biotechnology 1991, pp 6-13. By definition, both Kd and Kav values always lie within the range 0-1. The Kav value can advantageously be 0.6-0.95, e.g. 0.7-0.90 or 0.6-0.8, as measured with dextran of Mw 110 kDa as a probe molecule. An advantage of this is that the support has a large fraction of pores able to accommodate both the polypeptides/multimers of the invention and immunoglobulins binding to the polypeptides/multimers and to provide mass transport of the immunoglobulins to and from the binding sites.

The polypeptides or multimers may be attached to the support via conventional coupling techniques utilising e.g. thiol, amino and/or carboxy groups present in the ligand. Bisepoxides, epichlorohydrin, CNBr, N-hydroxysuccinimide (NHS) etc are well-known coupling reagents. Between the support and the polypeptide/multimer, a molecule known as a spacer can be introduced, which improves the availability of the polypeptide/multimer and facilitates the chemical coupling of the polypeptide/multimer to the support. Depending on the nature of the polypeptide/multimer and the coupling conditions, the coupling may be a multipoint coupling (e.g. via a plurality of lysines) or a single point coupling (e.g. via a single cysteine). Alternatively, the polypeptide/multimer may be attached to the support by non-covalent bonding, such as physical adsorption or biospecific adsorption.

In some embodiments the matrix comprises 5-25, such as 5-20 mg/ml, 5-15 mg/ml, 5-11 mg/ml or 6-11 mg/ml of the polypeptide or multimer coupled to the support. The amount of coupled polypeptide/multimer can be controlled by the concentration of polypeptide/multimer used in the coupling process, by the activation and coupling conditions used and/or by the pore structure of the support used. As a general rule the absolute binding capacity of the matrix increases with the amount of coupled polypeptide/multimer, at least up to a point where the pores become significantly constricted by the coupled polypeptide/multimer. The relative binding capacity per mg coupled polypeptide/multimer will decrease at high coupling levels, resulting in a cost-benefit optimum within the ranges specified above.

In certain embodiments the polypeptides or multimers are coupled to the support via thioether bonds. Methods for performing such coupling are well-known in this field and easily performed by the skilled person in this field using standard techniques and equipment. Thioether bonds are flexible and stable and generally suited for use in affinity chromatography. In particular when the thioether bond is via a terminal or near-terminal cysteine residue on the polypeptide or multimer, the mobility of the coupled polypeptide/multimer is enhanced which provides improved binding capacity and binding kinetics. In some embodiments the polypeptide/multimer is coupled via a C-terminal cysteine provided on the protein as described above. This allows for efficient coupling of the cysteine thiol to electrophilic groups, e.g. epoxide groups, halohydrin groups etc. on a support, resulting in a thioether bridge coupling.

In certain embodiments the support comprises a polyhydroxy polymer, such as a polysaccharide. Examples of polysaccharides include e.g. dextran, starch, cellulose, pullulan, agar, agarose etc. Polysaccharides are inherently hydrophilic with low degrees of nonspecific interactions, they provide a high content of reactive (activatable) hydroxyl groups and they are generally stable towards alkaline cleaning solutions used in bioprocessing.

In some embodiments the support comprises agar or agarose. The supports used in the present invention can easily be prepared according to standard methods, such as inverse suspension gelation (S Hjertén: Biochim Biophys Acta 79(2), 393-398 (1964). Alternatively, the base matrices are commercially available products, such as crosslinked agarose beads sold under the name of SEPHAROSE™ FF (GE Healthcare). In an embodiment, which is especially advantageous for large-scale separations, the support has been adapted to increase its rigidity using the methods described in U.S. Pat. No. 6,602,990 or 7,396,467, which are hereby incorporated by reference in their entirety, and hence renders the matrix more suitable for high flow rates.

In certain embodiments the support, such as a polysaccharide or agarose support, is crosslinked, such as with hydroxyalkyl ether crosslinks. Crosslinker reagents producing such crosslinks can be e.g. epihalohydrins like epichlorohydrin, diepoxides like butanediol diglycidyl ether, allylating reagents like allyl halides or allyl glycidyl ether. Crosslinking is beneficial for the rigidity of the support and improves the chemical stability. Hydroxyalkyl ether crosslinks are alkali stable and do not cause significant nonspecific adsorption.

Alternatively, the solid support is based on synthetic polymers, such as polyvinyl alcohol, polyhydroxyalkyl acrylates, polyhydroxyalkyl methacrylates, polyacrylamides, polymethacrylamides etc. In case of hydrophobic polymers, such as matrices based on divinyl and monovinyl-substituted benzenes, the surface of the matrix is often hydrophilised to expose hydrophilic groups as defined above to a surrounding aqueous liquid. Such polymers are easily produced according to standard methods, see e.g. "Styrene based polymer supports developed by suspension polymerization" (R Arshady: Chimica e L'Industria 70(9), 70-75 (1988)). Alternatively, a commercially available product, such as SOURCE™ (GE Healthcare) is used. In another alternative, the solid support according to the invention comprises a support of inorganic nature, e.g. silica, zirconium oxide etc.

In yet another embodiment, the solid support is in another form such as a surface, a chip, capillaries, or a filter (e.g. a membrane or a depth filter matrix).

As regards the shape of the matrix according to the invention, in one embodiment the matrix is in the form of a porous monolith. In an alternative embodiment, the matrix is in beaded or particle form that can be porous or non-porous. Matrices in beaded or particle form can be used as a packed bed or in a suspended form. Suspended forms include those known as expanded beds and pure suspensions, in which the particles or beads are free to move. In case of monoliths, packed bed and expanded beds, the separation procedure commonly follows conventional chromatography with a concentration gradient. In case of pure suspension, batchwise mode will be used.

In a sixth aspect, the present invention discloses a method of isolating an immunoglobulin, wherein a separation matrix as disclosed above is used.

In certain embodiments, the method comprises the steps of:
a) contacting a liquid sample comprising an immunoglobulin with a separation matrix as disclosed above,
b) washing said separation matrix with a washing liquid,
c) eluting the immunoglobulin from the separation matrix with an elution liquid, and
d) cleaning the separation matrix with a cleaning liquid, which can alternatively be called a cleaning-in-place (CIP) liquid, e.g. with a contact (incubation) time of at least 10 min.

The method may also comprise steps of, before step a), providing an affinity separation matrix according to any of the embodiments described above and providing a solution comprising an immunoglobulin and at least one other substance as a liquid sample and of, after step c), recovering the eluate and optionally subjecting the eluate to further separation steps, e.g. by anion or cation exchange chromatography, multimodal chromatography and/or hydrophobic interaction chromatography. Suitable compositions of the liquid sample, the washing liquid and the elution liquid, as well as the general conditions for performing the separation are well known in the art of affinity chromatography and in particular in the art of Protein A chromatography. The liquid sample comprising an Fc-containing protein and at least one other substance may comprise host cell proteins (HCP), such as CHO cell, *E coli* or yeast proteins. Contents of CHO cell and *E coli* proteins can conveniently be determined by immunoassays directed towards these proteins, e.g. the CHO HCP or *E coli* HCP ELISA kits from *Cygnus* Technologies. The host cell proteins or CHO cell/*E coli* proteins may be desorbed during step b).

The elution may be performed by using any suitable solution used for elution from Protein A media. This can e.g. be a solution or buffer with pH 5 or lower, such as pH 2.5-5 or 3-5. It can also in some cases be a solution or buffer with pH 11 or higher, such as pH 11-14 or pH 11-13. In some embodiments the elution buffer or the elution buffer gradient comprises at least one mono- di- or trifunctional carboxylic acid or salt of such a carboxylic acid. In certain embodiments the elution buffer or the elution buffer gradient comprises at least one anion species selected from the group consisting of acetate, citrate, glycine, succinate, phosphate, and formiate.

In some embodiments, the cleaning liquid is alkaline, such as with a pH of 13-14. Such solutions provide efficient cleaning of the matrix, in particular at the upper end of the interval In certain embodiments, the cleaning liquid comprises 0.1-2.0 M NaOH or KOH, such as 0.5-2.0 or 0.5-1.0 M NaOH or KOH. These are efficient cleaning solutions, and in particular so when the NaOH or KOH concentration is above 0.1 M or at least 0.5 M. The high stability of the polypeptides of the invention enables the use of such strongly alkaline solutions.

The method may also include a step of sanitizing the matrix with a sanitization liquid, which may e.g. comprise a peroxide, such as hydrogen peroxide and/or a peracid, such as peracetic acid or performic acid.

In some embodiments, steps a)-d) are repeated at least 10 times, such as at least 50 times, 50-200, 50-300 or 50-500 times. This is important for the process economy in that the matrix can be re-used many times.

Steps a)-c) can also be repeated at least 10 times, such as at least 50 times, 50-200, 50-300 or 50-500 times, with step d) being performed after a plurality of instances of step c), such that step d) is performed at least 10 times, such as at least 50 times. Step d) can e.g. be performed every second to twentieth instance of step c).

EXAMPLES

Mutagenesis of Protein

Site-directed mutagenesis was performed by a two-step PCR using oligonucleotides coding for the mutations. As template a plasmid containing a single domain of either Z, B or C was used. The PCR fragments were ligated into an *E. coli* expression vector. DNA sequencing was used to verify the correct sequence of inserted fragments.

To form multimers of mutants an Acc I site located in the starting codons (GTA GAC) of the B, C or Z domain was used, corresponding to amino acids VD. The vector for the monomeric domain was digested with Acc I and phosphatase treated. Acc I sticky-ends primers were designed, specific for each variant, and two overlapping PCR products were generated from each template. The PCR products were purified and the concentration was estimated by comparing the PCR products on a 2% agarose gel. Equal amounts of the pair wise PCR products were hybridized (90° C.->25° C. in 45 min) in ligation buffer. The resulting product consists approximately to ¼ of fragments likely to be ligated into an Acc I site (correct PCR fragments and/or the digested vector). After ligation and transformation colonies were PCR screened to identify constructs containing the desired mutant. Positive clones were verified by DNA sequencing.

Construct Expression and Purification

The constructs were expressed in the bacterial periplasm by fermentation of *E. coli* K12 in standard media. After fermentation the cells were heat-treated to release the periplasm content into the media. The constructs released into the medium were recovered by microfiltration with a membrane having a 0.2 µm pore size.

Each construct, now in the permeate from the filtration step, was purified by affinity. The permeate was loaded onto a chromatography medium containing immobilized IgG (IgG Sepharose 6FF, GE Healthcare). The loaded product was washed with phosphate buffered saline and eluted by lowering the pH.

The elution pool was adjusted to a neutral pH (pH 8) and reduced by addition of dithiothreitol. The sample was then loaded onto an anion exchanger. After a wash step the construct was eluted in a NaCl gradient to separate it from any contaminants. The elution pool was concentrated by ultrafiltration to 40-50 mg/ml. It should be noted that the successful affinity purification of a construct on an immobilized IgG medium indicates that the construct in question has a high affinity to IgG.

The purified ligands were analyzed with RPC LC-MS to determine the purity and to ascertain that the molecular weight corresponded to the expected (based on the amino acid sequence).

Example 1

The purified monomeric ligands listed in Table 1, further comprising an AQGT leader sequence at the N-terminus and a cysteine at the C terminus, were immobilized on Biacore CM5 sensor chips (GE Healthcare, Sweden), using the amine coupling kit of GE Healthcare (for carbodiimide coupling of amines on the carboxymethyl groups on the chip) in an amount sufficient to give a signal strength of about 200-1500 RU in a Biacore surface plasmon resonance (SPR) instrument (GE Healthcare, Sweden). To follow the IgG binding capacity of the immobilized surface 1 mg/ml human polyclonal IgG (Gammanorm) was flowed over the chip and the signal strength (proportional to the amount of binding) was noted. The surface was then cleaned-in-place (CIP), i.e. flushed with 500 mM NaOH for 10 minutes at room temperature (22+/−2° C.). This was repeated for 96-100 cycles and the immobilized ligand alkaline stability was followed as the remaining IgG binding capacity (signal strength) after each cycle. The results are shown in Table 1 and indicate that at least the ligands Zvar(D37E)1, Zvar (A42R)1, Zvar(S33K,D37E,A42R,N43A,L44I,K50R, L51Y)1, Zvar(H18K,S33K,D37E,A42R,N43A,L44I,K50R, L51Y)1, Zvar(N11K,H18K,S33K,D37E,A42R,N43A,L44I, K50R,L51Y)1, Zvar(Q9A,N11K,H18K,S33K,D37E,A42R, N43A,L44I,K50R,L51Y)1, Zvar(N11K, H18K, D37E, A42R, N43A, L44I)1, Zvar(Q9A, N11K, H18K, D37E, A42R, N43A, L44I)1 and Zvar(Q9A, N11K, H18K, D37E, A42R, N43A, L44I, K50R)1 have an improved alkali stability compared to the parental structure Zvar1, used as the reference.

TABLE 1

Monomeric ligands, evaluated by Biacore (0.5M NaOH).

| Ligand | Sequence | Capacity after 96-100 cycles | Reference capacity after 96-100 cycles | Capacity relative to reference |
|---|---|---|---|---|
| Zvar(D37E)1 | SEQ ID NO 9 | 57% | 47% | 1.21 |
| Zvar(A42R)1 | SEQ ID NO 10 | 56% | 47% | 1.19 |
| Zvar(S33K, D37E, A42R, N43A, L44I, K50R, L51Y)1 | SEQ ID NO 11 | 49% | 46% | 1.07 |
| Zvar(H18K, S33K, D37E, A42R, N43A, L44I, K50R, L51Y)1 | SEQ ID NO 12 | 48% | 46% | 1.04 |

TABLE 1-continued

Monomeric ligands, evaluated by Biacore (0.5M NaOH).

| Ligand | Sequence | Capacity after 96-100 cycles | Reference capacity after 96-100 cycles | Capacity relative to reference |
|---|---|---|---|---|
| Zvar(N11K, H18K, S33K, D37E, A42R, N43A, L44I, K50R, L51Y)1 | SEQ ID NO 13 | 67% | 46% | 1.46 |
| Zvar(Q9A, N11K, H18K, S33K, D37E, A42R, N43A, L44I, K50R, L51Y)1 | SEQ ID NO 14 | 59% | 46% | 1.28 |
| Zvar(N11K, H18K, D37E, A42R, N43A, L44I)1 | SEQ ID NO 15 | 59% | 45% | 1.31 |
| Zvar(Q9A, N11K, H18K, D37E, A42R, N43A, L44I)1 | SEQ ID NO 16 | 63% | 45% | 1.40 |
| Zvar(Q9A, N11K, H18K, D37E, A42R, N43A, L44I, K50R)1 | SEQ ID NO 17 | 67% | 45% | 1.49 |

Example 2

The purified tetrameric ligands listed in Table 2 were immobilized on Biacore CM5 sensor chips (GE Healthcare, Sweden), using the amine coupling kit of GE Healthcare (for carbodiimide coupling of amines on the carboxymethyl groups on the chip) in an amount sufficient to give a signal strength of about 200-1500 RU in a Biacore instrument (GE Healthcare, Sweden). To follow the IgG binding capacity of the immobilized surface 1 mg/ml human polyclonal IgG (Gammanorm) was flowed over the chip and the signal strength (proportional to the amount of binding) was noted. The surface was then cleaned-in-place (CIP), i.e. flushed with 500 mM NaOH for 10 minutes at room temperature (22+/−2° C.). This was repeated for 300 cycles and the immobilized ligand alkaline stability was followed as the remaining IgG binding capacity (signal strength) after each cycle. The results are shown in Table and in FIG. 2 and indicate that at least the ligands Zvar(Q9A,N11E,D37E, Q40V,A42K,N43A,L44I)4 and Zvar(Q9A,N11E,D37E, Q40V,A42R,N43A,L44I)4 have an improved alkali stability compared to the parental structure Zvar4, which was used as a reference.

TABLE 2

Tetrameric and hexameric ligands, evaluated by Biacore (0.5M NaOH).

| Ligand | SEQ ID NO: | Remaining capacity 100 cycles (%) | Capacity relative to ref. 100 cycles |
|---|---|---|---|
| Zvar4 | 19 | 67 | 1 |
| Zvar(Q9A, N11E, D37E, Q40V, A42K, N43A, L44I)4 | 22 | 81 | 1.13 |
| Zvar(Q9A, N11E, D37E, Q40V, A42R, N43A, L44I)4 | 23 | 84 | 1.17 |

Example 3

The purified tetrameric ligands of Table 3 (all with an additional N-terminal cysteine) were immobilized on agarose beads using the methods described below and assessed for capacity and stability. The results are shown in Table 2.

TABLE 3

Matrices with tetrametric ligands, evaluated in columns (0.5M NaOH).

| Ligand | SEQ ID NO. | Ligand content (mg/ml) | Initial IgG capacity Qb10 (mg/ml) | Remaining IgG capacity after six 4 h cycles (mg/ml) | Remaining IgG capacity after six 4 h cycles (%) | Capacity retention relative to ref. after six 4 h cycles |
|---|---|---|---|---|---|---|
| Zvar4 | 19 | 7 | 52.5 | 36.5 | 60 | 1 |
| Zvar4 | 19 | 12 | 61.1 | 43.4 | 71 | 1 |
| Zvar(N11K, H18K, S33K, D37E, A42R, N43A, L44I, K50R, L51Y)4 | 20 | 9.7 | 56.3 | 52.0 | 92 | 1.42 |
| Zvar(Q9A, N11K, H18K, D37E, A42R)4 | 21 | 10.8 | 56.9 | 52.5 | 92 | 1.21 |
| Zvar4 | 19 | 7 | 52.5 | 36.5 | 60 | 1 |
| Zvar(N11K, H18K, S33K, D37E, A42R, N43A, L44I, K50R, L51Y)4 | 20 | 9.7 | 56.3 | 52.0 | 92 | 1.42 |
| Zvar(Q9A, N11K, H18K, D37E, A42R)4 | 21 | 10.8 | 56.9 | 52.5 | 92 | 1.21 |

Activation

The base matrix used was rigid cross-linked agarose beads of 85 micrometers (volume-weighted, d50V) median diameter, prepared according to the methods of U.S. Pat. No. 6,602,990 and with a pore size corresponding to an inverse gel filtration chromatography Kav value of 0.70 for dextran of Mw 110 kDa, according to the methods described in Gel Filtration Principles and Methods, Pharmacia LKB Biotechnology 1991, pp 6-13.

25 mL (g) of drained base matrix, 10.0 mL distilled water and 2.02 g NaOH (s) was mixed in a 100 mL flask with mechanical stirring for 10 min at 25° C. 4.0 mL of epichlorohydrin was added and the reaction progressed for 2 hours. The activated gel was washed with 10 gel sediment volumes (GV) of water.

Coupling

To 20 mL of ligand solution (50 mg/mL) in a 50 ml Falcon tube, 169 mg NaHCO$_3$, 21 mg Na$_2$CO$_3$, 175 mg NaCl and 7 mg EDTA, was added. The Falcon tube was placed on a roller table for 5-10 min, and then 77 mg of DTE was added. Reduction proceeded for >45 min. The ligand solution was then desalted on a PD10 column packed with Sephadex G-25. The ligand content in the desalted solution was determined by measuring the 276 nm UV absorption.

The activated gel was washed with 3-5 GV {0.1 M phosphate/1 mM EDTA pH 8.6} and the ligand was then coupled according to the method described in U.S. Pat. No. 6,399,750. All buffers used in the experiments had been degassed by nitrogen gas for at least 5-10 min. The ligand content of the gels could be controlled by varying the amount and concentration of the ligand solution.

After immobilization the gels were washed 3×GV with distilled water. The gels+1 GV {0.1 M phosphate/1 mM EDTA/10% thioglycerol pH 8.6} was mixed and the tubes were left in a shaking table at room temperature overnight. The gels were then washed alternately with 3×GV {0.1 M TRIS/0.15 M NaCl pH 8.6} and 0.5 M HAc and then 8-10×GV with distilled water. Gel samples were sent to an external laboratory for amino acid analysis and the ligand content (mg/ml gel) was calculated from the total amino acid content.

Protein

Gammanorm 165 mg/ml (Octapharma), diluted to 2 mg/ml in Equilibration buffer.

Equilibration Buffer

PBS Phosphate buffer 10 mM+0.14 M NaCl+0.0027 M KCl, pH 7.4 (Medicago)

Adsorption Buffer

PBS Phosphate buffer 10 mM+0.14 M NaCl+0.0027 M KCl, pH 7.4 (Medicago)

Elution Buffers 100 mM acetate pH 2.9

Dynamic Binding Capacity 2 ml of resin was packed in TRICORN 5 100 columns. The breakthrough capacity was determined with an ÄKTA-Explorer 10 system at a residence time of 6 minutes. Equilibration buffer was run through the bypass column until a stable baseline was obtained. This was done prior to auto zeroing. Sample was applied to the column until a 100% UV signal was obtained. Then, equilibration buffer was applied again until a stable baseline was obtained.

Sample was loaded onto the column until a UV signal of 85% of maximum absorbance was reached. The column was then washed with 5 column volumes (CV) equilibration buffer at flow rate 0.5 ml/min. The protein was eluted with 5 CV elution buffer at a flow rate of 0.5 ml/min. Then the column was cleaned with 0.5M NaOH at flow rate 0.2 ml/min and re-equilibrated with equilibration buffer.

For calculation of breakthrough capacity at 10%, the equation below was used. That is the amount of IgG that is loaded onto the column until the concentration of IgG in the column effluent is 10% of the IgG concentration in the feed.

$$q_{10\%} = \frac{C_0}{V_c}\left[V_{app} - V_{sys} - \int_{V_{sys}}^{V_{app}} \frac{A(V) - A_{sub}}{A_{100\%} - A_{sub}} * dv\right]$$

$A_{100\%}$=100% UV signal;
$A_{sub}$=absorbance contribution from non-binding IgG subclass;
$A(V)$=absorbance at a given applied volume;
$V_c$=column volume;
$V_{app}$=volume applied until 10% breakthrough;
$V_{sys}$=system dead volume;
$C_0$=feed concentration.

The dynamic binding capacity (DBC) at 10% breakthrough was calculated. The dynamic binding capacity (DBC) was calculated for 10 and 80% breakthrough.

CIP—0.5 M NaOH

The 10% breakthrough DBC (Qb10) was determined both before and after repeated exposures to alkaline cleaning solutions. Each cycle included a CIP step with 0.5 M NaOH pumped through the column at a rate of 0.5/min for 20 min, after which the column was left standing for 4 h. The exposure took place at room temperature (22+/−2° C.). After this incubation, the column was washed with equilibration buffer for 20 min at a flow rate of 0.5 ml/min. Table 4 shows the remaining capacity after six 4 h cycles (i.e. 24 h cumulative exposure time to 0.5 M NaOH), both in absolute numbers and relative to the initial capacity.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

What is claimed is:

1. An Fc-binding polypeptide comprising a mutant of an Fc-binding domain of *Staphylococcus* Protein A (SpA) as defined by a consensus sequence KEX$_1$QX$_2$AFYEILX$_3$LPNLTEEQRNAFIQX$_6$LKDX$_7$PS-QSX$_9$X$_{10}$X$_{11}$LAEAKX$_{12}$X$_{13}$NDAQAPK (SEQ ID NO:28), wherein X$_7$ is E and X$_9$ is R, and wherein individually of each other at least one of X$_1$, X$_2$, X$_3$, X$_6$, X$_{10}$, X$_{11}$, X$_{12}$, and X$_{13}$ is substituted as follows:
X$_1$=A or else Q,
X$_2$=K or else or N,
X$_3$=K or else H,
X$_6$=K or else S,
X$_{10}$=A or else N,
X$_{11}$=I or else L,
X$_{12}$=R or else K,
X$_{13}$=Y or else L,
and wherein the mutant binds the Fc domain of an antibody and has improved alkaline stability compared to the amino acid sequence of SEQ ID NO:7, wherein the alkaline stability is improved as measured by the remaining IgG-binding capacity after 24 or 25 h incubation in 0.5 M or 1.0 M aqueous NaOH at 22+/−2° C.

2. The polypeptide of claim 1, wherein X$_1$=A.
3. The polypeptide of claim 1, wherein X$_2$=K.
4. The polypeptide of claim 1, wherein X$_3$=K.
5. The polypeptide of claim 1, wherein X$_{10}$=N.
6. The polypeptide of claim 1, wherein X$_{11}$=L.
7. The polypeptide of claim 1, wherein X$_{12}$=K.
8. The polypeptide of claim 1, wherein X$_{13}$=Y.
9. The polypeptide of claim 1, wherein the mutant is selected from the group consisting of SEQ ID NO:9, SEQ ID NO: 10, SEQ ID NO:11, SEQ ID NO: 12, SEQ ID NO: 13, SEQ ID NO:14, SEQ ID NO:15, SEQ ID NO:16, and SEQ ID NO:17.
10. A multimer comprising or consisting essentially of a plurality of polypeptides as defined by claim 1.
11. The multimer of claim 10, wherein the polypeptides are linked by linkers comprising up to 15 amino acids.
12. The multimer of claim 10, which is a dimer, trimer, tetramer, pentamer, hexamer, heptamer, octamer or nonamer.
13. The multimer of claim 10, which comprises a sequence as defined by SEQ ID NO: 20, SEQ ID NO:21, SEQ ID NO:22 and SEQ ID NO:23.

* * * * *

SEQUENCE LISTING

<160> NUMBER OF SEQ ID NOS: 28

<210> SEQ ID NO 1
<211> LENGTH: 51
<212> TYPE: PRT

<213> ORGANISM: Staphylococcus aureus

<400> SEQUENCE: 1

Ala Gln Gln Asn Ala Phe Tyr Gln Val Leu Asn Met Pro Asn Leu Asn
1               5                   10                  15
Ala Asp Gln Arg Asn Gly Phe Ile Gln Ser Leu Lys Asp Asp Pro Ser
                20                  25                  30
Gln Ser Ala Asn Val Leu Gly Glu Ala Gln Lys Leu Asn Asp Ser Gln
            35                  40                  45
Ala Pro Lys
        50

<210> SEQ ID NO 2
<211> LENGTH: 61
<212> TYPE: PRT
<213> ORGANISM: Staphylococcus aureus

<400> SEQUENCE: 2

Ala Asp Ala Gln Gln Asn Lys Phe Asn Lys Asp Gln Gln Ser Ala Phe
1               5                   10                  15
Tyr Glu Ile Leu Asn Met Pro Asn Leu Asn Glu Glu Gln Arg Asn Gly
                20                  25                  30
Phe Ile Gln Ser Leu Lys Asp Asp Pro Ser Gln Ser Thr Asn Val Leu
            35                  40                  45
Gly Glu Ala Lys Lys Leu Asn Glu Ser Gln Ala Pro Lys
        50                  55                  60

<210> SEQ ID NO 3
<211> LENGTH: 58
<212> TYPE: PRT
<213> ORGANISM: Staphylococcus aureus

<400> SEQUENCE: 3

Ala Asp Asn Asn Phe Asn Lys Glu Gln Gln Asn Ala Phe Tyr Glu Ile
1               5                   10                  15
Leu Asn Met Pro Asn Leu Asn Glu Glu Gln Arg Asn Gly Phe Ile Gln
                20                  25                  30
Ser Leu Lys Asp Asp Pro Ser Gln Ser Ala Asn Leu Leu Ala Glu Ala
            35                  40                  45
Lys Lys Leu Asn Glu Ser Gln Ala Pro Lys
        50                  55

<210> SEQ ID NO 4
<211> LENGTH: 58
<212> TYPE: PRT
<213> ORGANISM: Staphylococcus aureus

<400> SEQUENCE: 4

Ala Asp Asn Lys Phe Asn Lys Glu Gln Gln Asn Ala Phe Tyr Glu Ile
1               5                   10                  15
Leu His Leu Pro Asn Leu Asn Glu Glu Gln Arg Asn Gly Phe Ile Gln
                20                  25                  30
Ser Leu Lys Asp Asp Pro Ser Gln Ser Ala Asn Leu Leu Ala Glu Ala
            35                  40                  45
Lys Lys Leu Asn Asp Ala Gln Ala Pro Lys
        50                  55

<210> SEQ ID NO 5
<211> LENGTH: 58

<212> TYPE: PRT
<213> ORGANISM: Staphylococcus aureus

<400> SEQUENCE: 5

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 6
<211> LENGTH: 58
<212> TYPE: PRT
<213> ORGANISM: Escherichia coli

<400> SEQUENCE: 6

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 7
<211> LENGTH: 58
<212> TYPE: PRT
<213> ORGANISM: Escherichia coli

<400> SEQUENCE: 7

Val Asp Ala Lys Phe Asp Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 8
<211> LENGTH: 58
<212> TYPE: PRT
<213> ORGANISM: Staphylococcus aureus

<400> SEQUENCE: 8

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
        35                  40                  45

Lys Lys Leu Asn Glu Ser Gln Ala Pro Lys
    50                  55

<210> SEQ ID NO 9

```
<211> LENGTH: 58
<212> TYPE: PRT
<213> ORGANISM: Escherichia coli

<400> SEQUENCE: 9

Val Asp Ala Lys Phe Asp Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Glu Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 10
<211> LENGTH: 58
<212> TYPE: PRT
<213> ORGANISM: Escherichia coli

<400> SEQUENCE: 10

Val Asp Ala Lys Phe Asp Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Gln Ser Arg Asn Leu Leu Ala Glu Ala
        35                  40                  45

Lys Lys Leu Asn Asp Ala Gln Ala Pro Lys
    50                  55

<210> SEQ ID NO 11
<211> LENGTH: 58
<212> TYPE: PRT
<213> ORGANISM: Escherichia coli

<400> SEQUENCE: 11

Val Asp Ala Lys Phe Asp Lys Glu Gln Gln Asn Ala Phe Tyr Glu Ile
1               5                   10                  15

Leu His Leu Pro Asn Leu Thr Glu Glu Gln Arg Asn Ala Phe Ile Gln
            20                  25                  30

Lys Leu Lys Asp Glu Pro Ser Gln Ser Arg Ala Ile Leu Ala Glu Ala
        35                  40                  45

Lys Arg Tyr Asn Asp Ala Gln Ala Pro Lys
    50                  55

<210> SEQ ID NO 12
<211> LENGTH: 58
<212> TYPE: PRT
<213> ORGANISM: Escherichia coli

<400> SEQUENCE: 12

Val Asp Ala Lys Phe Asp Lys Glu Gln Gln Asn Ala Phe Tyr Glu Ile
1               5                   10                  15

Leu Lys Leu Pro Asn Leu Thr Glu Glu Gln Arg Asn Ala Phe Ile Gln
            20                  25                  30

Lys Leu Lys Asp Glu Pro Ser Gln Ser Arg Ala Ile Leu Ala Glu Ala
        35                  40                  45

Lys Arg Tyr Asn Asp Ala Gln Ala Pro Lys
    50                  55
```

```
<210> SEQ ID NO 13
<211> LENGTH: 58
<212> TYPE: PRT
<213> ORGANISM: Escherichia coli

<400> SEQUENCE: 13

Val Asp Ala Lys Phe Asp Lys Glu Gln Gln Lys Ala Phe Tyr Glu Ile
1               5                   10                  15

Leu Lys Leu Pro Asn Leu Thr Glu Glu Gln Arg Asn Ala Phe Ile Gln
            20                  25                  30

Lys Leu Lys Asp Glu Pro Ser Gln Ser Arg Ala Ile Leu Ala Glu Ala
        35                  40                  45

Lys Arg Tyr Asn Asp Ala Gln Ala Pro Lys
    50                  55

<210> SEQ ID NO 14
<211> LENGTH: 58
<212> TYPE: PRT
<213> ORGANISM: Escherichia coli

<400> SEQUENCE: 14

Val Asp Ala Lys Phe Asp Lys Glu Ala Gln Lys Ala Phe Tyr Glu Ile
1               5                   10                  15

Leu Lys Leu Pro Asn Leu Thr Glu Glu Gln Arg Ala Ala Phe Ile Gln
            20                  25                  30

Lys Leu Lys Asp Glu Pro Ser Gln Ser Arg Ala Ile Leu Ala Glu Ala
        35                  40                  45

Lys Arg Tyr Asn Asp Ala Gln Ala Pro Lys
    50                  55

<210> SEQ ID NO 15
<211> LENGTH: 58
<212> TYPE: PRT
<213> ORGANISM: Escherichia coli

<400> SEQUENCE: 15

Val Asp Ala Lys Phe Asp Lys Glu Gln Gln Lys Ala Phe Tyr Glu Ile
1               5                   10                  15

Leu Lys Leu Pro Asn Leu Thr Glu Glu Gln Arg Asn Ala Phe Ile Gln
            20                  25                  30

Ser Leu Lys Asp Glu Pro Ser Gln Ser Arg Ala Ile Leu Ala Glu Ala
        35                  40                  45

Lys Lys Leu Asn Asp Ala Gln Ala Pro Lys
    50                  55

<210> SEQ ID NO 16
<211> LENGTH: 58
<212> TYPE: PRT
<213> ORGANISM: Escherichia coli

<400> SEQUENCE: 16

Val Asp Ala Lys Phe Asp Lys Glu Ala Gln Lys Ala Phe Tyr Glu Ile
1               5                   10                  15

Leu Lys Leu Pro Asn Leu Thr Glu Glu Gln Arg Asn Ala Phe Ile Gln
            20                  25                  30

Ser Leu Lys Asp Glu Pro Ser Gln Ser Arg Ala Ile Leu Ala Glu Ala
        35                  40                  45

Lys Lys Leu Asn Asp Ala Gln Ala Pro Lys
    50                  55
```

-continued

<210> SEQ ID NO 17
<211> LENGTH: 58
<212> TYPE: PRT
<213> ORGANISM: Escherichia coli

<400> SEQUENCE: 17

Val Asp Ala Lys Phe Asp Lys Glu Ala Gln Lys Ala Phe Tyr Glu Ile
1               5                   10                  15

Leu Lys Leu Pro Asn Leu Thr Glu Glu Gln Arg Asn Ala Phe Ile Gln
            20                  25                  30

Ser Leu Lys Asp Glu Pro Ser Gln Ser Arg Ala Ile Leu Ala Glu Ala
        35                  40                  45

Lys Arg Leu Asn Asp Ala Gln Ala Pro Lys
    50                  55

<210> SEQ ID NO 18
<211> LENGTH: 58
<212> TYPE: PRT
<213> ORGANISM: Escherichia coli

<400> SEQUENCE: 18

Val Asp Ala Lys Phe Asp Lys Glu Ala Gln Lys Ala Phe Tyr Glu Ile
1               5                   10                  15

Leu Lys Leu Pro Asn Leu Thr Glu Glu Gln Arg Asn Ala Phe Ile Gln
            20                  25                  30

Ser Leu Lys Asp Glu Pro Ser Gln Ser Arg Asn Leu Leu Ala Glu Ala
        35                  40                  45

Lys Lys Leu Asn Asp Ala Gln Ala Pro Lys
    50                  55

<210> SEQ ID NO 19
<211> LENGTH: 237
<212> TYPE: PRT
<213> ORGANISM: Escherichia coli

<400> SEQUENCE: 19

Ala Gln Gly Thr Val Asp Ala Lys Phe Asp Lys Glu Gln Gln Asn Ala
1               5                   10                  15

Phe Tyr Glu Ile Leu His Leu Pro Asn Leu Thr Glu Glu Gln Arg Asn
            20                  25                  30

Ala Phe Ile Gln Ser Leu Lys Asp Asp Pro Ser Gln Ser Ala Asn Leu
        35                  40                  45

Leu Ala Glu Ala Lys Lys Leu Asn Asp Ala Gln Ala Pro Lys Val Asp
    50                  55                  60

Ala Lys Phe Asp Lys Glu Gln Gln Asn Ala Phe Tyr Glu Ile Leu His
65                  70                  75                  80

Leu Pro Asn Leu Thr Glu Glu Gln Arg Asn Ala Phe Ile Gln Ser Leu
                85                  90                  95

Lys Asp Asp Pro Ser Gln Ser Ala Asn Leu Leu Ala Glu Ala Lys Lys
            100                 105                 110

Leu Asn Asp Ala Gln Ala Pro Lys Val Asp Ala Lys Phe Asp Lys Glu
        115                 120                 125

Gln Gln Asn Ala Phe Tyr Glu Ile Leu His Leu Pro Asn Leu Thr Glu
    130                 135                 140

Glu Gln Arg Asn Ala Phe Ile Gln Ser Leu Lys Asp Asp Pro Ser Gln
145                 150                 155                 160

Ser Ala Asn Leu Leu Ala Glu Ala Lys Lys Leu Asn Asp Ala Gln Ala
            165                 170                 175

Pro Lys Val Asp Ala Lys Phe Asp Lys Glu Gln Gln Asn Ala Phe Tyr
            180                 185                 190

Glu Ile Leu His Leu Pro Asn Leu Thr Glu Glu Gln Arg Asn Ala Phe
            195                 200                 205

Ile Gln Ser Leu Lys Asp Asp Pro Ser Gln Ser Ala Asn Leu Leu Ala
            210                 215                 220

Glu Ala Lys Lys Leu Asn Asp Ala Gln Ala Pro Lys Cys
225                 230                 235

<210> SEQ ID NO 20
<211> LENGTH: 237
<212> TYPE: PRT
<213> ORGANISM: Escherichia coli

<400> SEQUENCE: 20

Ala Gln Gly Thr Val Asp Ala Lys Phe Asp Lys Glu Gln Gln Lys Ala
1               5                   10                  15

Phe Tyr Glu Ile Leu Lys Leu Pro Asn Leu Thr Glu Glu Gln Arg Asn
            20                  25                  30

Ala Phe Ile Gln Lys Leu Lys Asp Glu Pro Ser Gln Ser Arg Ala Ile
            35                  40                  45

Leu Ala Glu Ala Lys Arg Tyr Asn Asp Ala Gln Ala Pro Lys Val Asp
            50                  55                  60

Ala Lys Phe Asp Lys Glu Gln Gln Lys Ala Phe Tyr Glu Ile Leu Lys
65                  70                  75                  80

Leu Pro Asn Leu Thr Glu Glu Gln Arg Asn Ala Phe Ile Gln Lys Leu
                85                  90                  95

Lys Asp Glu Pro Ser Gln Ser Arg Ala Ile Leu Ala Glu Ala Lys Arg
            100                 105                 110

Tyr Asn Asp Ala Gln Ala Pro Lys Val Asp Ala Lys Phe Asp Lys Glu
            115                 120                 125

Gln Gln Lys Ala Phe Tyr Glu Ile Leu Lys Leu Pro Asn Leu Thr Glu
130                 135                 140

Glu Gln Arg Asn Ala Phe Ile Gln Lys Leu Lys Asp Glu Pro Ser Gln
145                 150                 155                 160

Ser Arg Ala Ile Leu Ala Glu Ala Lys Arg Tyr Asn Asp Ala Gln Ala
                165                 170                 175

Pro Lys Val Asp Ala Lys Phe Asp Lys Glu Gln Gln Lys Ala Phe Tyr
            180                 185                 190

Glu Ile Leu Lys Leu Pro Asn Leu Thr Glu Glu Gln Arg Asn Ala Phe
            195                 200                 205

Ile Gln Lys Leu Lys Asp Glu Pro Ser Gln Ser Arg Ala Ile Leu Ala
            210                 215                 220

Glu Ala Lys Arg Tyr Asn Asp Ala Gln Ala Pro Lys Cys
225                 230                 235

<210> SEQ ID NO 21
<211> LENGTH: 237
<212> TYPE: PRT
<213> ORGANISM: Escherichia coli

<400> SEQUENCE: 21

Ala Gln Gly Thr Val Asp Ala Lys Phe Asp Lys Glu Ala Gln Lys Ala
1               5                   10                  15

```
Phe Tyr Glu Ile Leu Lys Leu Pro Asn Leu Thr Glu Gln Arg Asn
            20                  25                  30

Ala Phe Ile Gln Ser Leu Lys Asp Glu Pro Ser Gln Ser Arg Asn Leu
        35                  40                  45

Leu Ala Glu Ala Lys Lys Leu Asn Asp Ala Gln Ala Pro Lys Val Asp
50                  55                  60

Ala Lys Phe Asp Lys Glu Ala Gln Lys Ala Phe Tyr Glu Ile Leu Lys
65                  70                  75                  80

Leu Pro Asn Leu Thr Glu Glu Gln Arg Asn Ala Phe Ile Gln Ser Leu
                85                  90                  95

Lys Asp Glu Pro Ser Gln Ser Arg Asn Leu Leu Ala Glu Ala Lys Lys
                100                 105                 110

Leu Asn Asp Ala Gln Ala Pro Lys Val Asp Ala Lys Phe Asp Lys Glu
            115                 120                 125

Ala Gln Lys Ala Phe Tyr Glu Ile Leu Lys Leu Pro Asn Leu Thr Glu
130                 135                 140

Glu Gln Arg Asn Ala Phe Ile Gln Ser Leu Lys Asp Glu Pro Ser Gln
145                 150                 155                 160

Ser Arg Asn Leu Leu Ala Glu Ala Lys Lys Leu Asn Asp Ala Gln Ala
                165                 170                 175

Pro Lys Val Asp Ala Lys Phe Asp Lys Glu Ala Gln Lys Ala Phe Tyr
            180                 185                 190

Glu Ile Leu Lys Leu Pro Asn Leu Thr Glu Gln Arg Asn Ala Phe
            195                 200                 205

Ile Gln Ser Leu Lys Asp Glu Pro Ser Gln Ser Arg Asn Leu Leu Ala
        210                 215                 220

Glu Ala Lys Lys Leu Asn Asp Ala Gln Ala Pro Lys Cys
225                 230                 235

<210> SEQ ID NO 22
<211> LENGTH: 237
<212> TYPE: PRT
<213> ORGANISM: Escherichia coli

<400> SEQUENCE: 22

Ala Gln Gly Thr Val Asp Ala Lys Phe Asp Lys Glu Ala Gln Glu Ala
1               5                   10                  15

Phe Tyr Glu Ile Leu His Leu Pro Asn Leu Thr Glu Gln Arg Asn
            20                  25                  30

Ala Phe Ile Gln Ser Leu Lys Asp Glu Pro Ser Val Ser Lys Ala Ile
        35                  40                  45

Leu Ala Glu Ala Lys Lys Leu Asn Asp Ala Gln Ala Pro Lys Val Asp
50                  55                  60

Ala Lys Phe Asp Lys Glu Ala Gln Glu Ala Phe Tyr Glu Ile Leu His
65                  70                  75                  80

Leu Pro Asn Leu Thr Glu Glu Gln Arg Asn Ala Phe Ile Gln Ser Leu
                85                  90                  95

Lys Asp Glu Pro Ser Val Ser Lys Ala Ile Leu Ala Glu Ala Lys Lys
                100                 105                 110

Leu Asn Asp Ala Gln Ala Pro Lys Val Asp Ala Lys Phe Asp Lys Glu
            115                 120                 125

Ala Gln Glu Ala Phe Tyr Glu Ile Leu His Leu Pro Asn Leu Thr Glu
130                 135                 140
```

Glu Gln Arg Asn Ala Phe Ile Gln Ser Leu Lys Asp Glu Pro Ser Val
145                 150                 155                 160

Ser Lys Ala Ile Leu Ala Glu Ala Lys Lys Leu Asn Asp Ala Gln Ala
            165                 170                 175

Pro Lys Val Asp Ala Lys Phe Asp Lys Glu Ala Gln Glu Ala Phe Tyr
        180                 185                 190

Glu Ile Leu His Leu Pro Asn Leu Thr Glu Glu Gln Arg Asn Ala Phe
            195                 200                 205

Ile Gln Ser Leu Lys Asp Glu Pro Ser Val Ser Lys Ala Ile Leu Ala
        210                 215                 220

Glu Ala Lys Lys Leu Asn Asp Ala Gln Ala Pro Lys Cys
225                 230                 235

<210> SEQ ID NO 23
<211> LENGTH: 237
<212> TYPE: PRT
<213> ORGANISM: Escherichia coli

<400> SEQUENCE: 23

Ala Gln Gly Thr Val Asp Ala Lys Phe Asp Lys Glu Ala Gln Glu Ala
1               5                   10                  15

Phe Tyr Glu Ile Leu His Leu Pro Asn Leu Thr Glu Glu Gln Arg Asn
            20                  25                  30

Ala Phe Ile Gln Ser Leu Lys Asp Glu Pro Ser Val Ser Arg Ala Ile
        35                  40                  45

Leu Ala Glu Ala Lys Lys Leu Asn Asp Ala Gln Ala Pro Lys Val Asp
    50                  55                  60

Ala Lys Phe Asp Lys Glu Ala Gln Glu Ala Phe Tyr Glu Ile Leu His
65                  70                  75                  80

Leu Pro Asn Leu Thr Glu Glu Gln Arg Asn Ala Phe Ile Gln Ser Leu
                85                  90                  95

Lys Asp Glu Pro Ser Val Ser Arg Ala Ile Leu Ala Glu Ala Lys Lys
            100                 105                 110

Leu Asn Asp Ala Gln Ala Pro Lys Val Asp Ala Lys Phe Asp Lys Glu
        115                 120                 125

Ala Gln Glu Ala Phe Tyr Glu Ile Leu His Leu Pro Asn Leu Thr Glu
    130                 135                 140

Glu Gln Arg Asn Ala Phe Ile Gln Ser Leu Lys Asp Glu Pro Ser Val
145                 150                 155                 160

Ser Arg Ala Ile Leu Ala Glu Ala Lys Lys Leu Asn Asp Ala Gln Ala
            165                 170                 175

Pro Lys Val Asp Ala Lys Phe Asp Lys Glu Ala Gln Glu Ala Phe Tyr
        180                 185                 190

Glu Ile Leu His Leu Pro Asn Leu Thr Glu Glu Gln Arg Asn Ala Phe
    195                 200                 205

Ile Gln Ser Leu Lys Asp Glu Pro Ser Val Ser Arg Ala Ile Leu Ala
        210                 215                 220

Glu Ala Lys Lys Leu Asn Asp Ala Gln Ala Pro Lys Cys
225                 230                 235

<210> SEQ ID NO 24
<211> LENGTH: 58
<212> TYPE: PRT
<213> ORGANISM: Escherichia coli

<400> SEQUENCE: 24

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Glu Pro Ser Val Ser Lys Ala Ile Leu Ala Glu Ala
        35                  40                  45

Lys Lys Leu Asn Asp Ala Gln Ala Pro Lys
    50                  55

<210> SEQ ID NO 25
<211> LENGTH: 58
<212> TYPE: PRT
<213> ORGANISM: Escherichia coli

<400> SEQUENCE: 25

Val Asp Ala Lys Phe Asp Lys Glu Ala Gln Glu Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Glu Pro Ser Val Ser Arg Ala Ile Leu Ala Glu Ala
        35                  40                  45

Lys Lys Leu Asn Asp Ala Gln Ala Pro Lys
    50                  55

<210> SEQ ID NO 26
<211> LENGTH: 52
<212> TYPE: PRT
<213> ORGANISM: Escherichia coli

<400> SEQUENCE: 26

Lys Glu Gln Gln Asn Ala Phe Tyr Glu Ile Leu His Leu Pro Asn Leu
1               5                   10                  15

Thr Glu Glu Gln Arg Asn Ala Phe Ile Gln Ser Leu Lys Asp Asp Pro
            20                  25                  30

Ser Gln Ser Ala Asn Leu Leu Ala Glu Ala Lys Lys Leu Asn Asp Ala
        35                  40                  45

Gln Ala Pro Lys
    50

<210> SEQ ID NO 27
<211> LENGTH: 52
<212> TYPE: PRT
<213> ORGANISM: Staphylococcus aureus

<400> SEQUENCE: 27

Lys Glu Gln Gln Asn Ala Phe Tyr Glu Ile Leu His Leu Pro Asn Leu
1               5                   10                  15

Thr Glu Glu Gln Arg Asn Gly Phe Ile Gln Ser Leu Lys Asp Asp Pro
            20                  25                  30

Ser Val Ser Lys Glu Ile Leu Ala Glu Ala Lys Lys Leu Asn Asp Ala
        35                  40                  45

Gln Ala Pro Lys
    50

<210> SEQ ID NO 28
<211> LENGTH: 52
<212> TYPE: PRT

```
<213> ORGANISM: Escherichia coli
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (36)..(38)
<223> OTHER INFORMATION: Xaa can be any naturally occurring amino acid
<220> FEATURE:
<221> NAME/KEY: misc_feature
<222> LOCATION: (44)..(45)
<223> OTHER INFORMATION: Xaa can be any naturally occurring amino acid

<400> SEQUENCE: 28

Lys Glu Xaa Gln Xaa Ala Phe Tyr Glu Ile Leu Xaa Leu Pro Asn Leu
1               5                   10                  15

Thr Glu Glu Gln Arg Xaa Xaa Phe Ile Gln Xaa Leu Lys Asp Xaa Pro
                20                  25                  30

Ser Xaa Ser Xaa Xaa Xaa Leu Ala Glu Ala Lys Xaa Xaa Asn Asp Ala
            35                  40                  45

Gln Ala Pro Lys
    50
```